(12) United States Patent
Walsh et al.

(10) Patent No.: US 8,609,364 B2
(45) Date of Patent: Dec. 17, 2013

(54) METHODS FOR ANTIMICROBIAL RESISTANCE DETERMINATION

(75) Inventors: John Walsh, Durham, NC (US); Jones Hyman, Wake Forest, NC (US)

(73) Assignee: bioMérieux, Inc., Durham, NC (US)

( * ) Notice: Subject to any disclaimer, the term of this patent is extended or adjusted under 35 U.S.C. 154(b) by 0 days.

(21) Appl. No.: 12/774,947

(22) Filed: May 6, 2010

(65) Prior Publication Data

US 2010/0285447 A1    Nov. 11, 2010

Related U.S. Application Data

(60) Provisional application No. 61/215,594, filed on May 7, 2009.

(51) Int. Cl.
   *C12Q 1/25* (2006.01)
(52) U.S. Cl.
   USPC .............. 435/32; 435/29; 435/5; 435/6.13; 435/6.18
(58) Field of Classification Search
   None
   See application file for complete search history.

(56) References Cited

U.S. PATENT DOCUMENTS

| | | | |
|---|---|---|---|
| 4,693,972 A * | 9/1987 | Mansour et al. | 435/34 |
| 4,868,130 A * | 9/1989 | Hargreaves | 436/526 |
| 5,716,829 A | 2/1998 | Rosok et al. | |
| 6,051,395 A | 4/2000 | Rocco | |
| 6,156,507 A | 12/2000 | Hiramatsu et al. | |
| 6,503,709 B1 * | 1/2003 | Bekkaoui et al. | 435/5 |
| 7,632,657 B2 * | 12/2009 | Rambach et al. | 435/32 |
| 2002/0076722 A1 * | 6/2002 | Neyfakh et al. | 435/6 |
| 2004/0265994 A1 * | 12/2004 | Brahmbhatt et al. | 435/325 |
| 2006/0110787 A1 | 5/2006 | Walker | |
| 2010/0197649 A1 * | 8/2010 | Cheung et al. | 514/192 |
| 2011/0003306 A1 * | 1/2011 | Thrippleton et al. | 435/6 |
| 2011/0204220 A1 * | 8/2011 | van Wuijckhuijse et al. | 250/282 |
| 2011/0250202 A1 * | 10/2011 | Cote et al. | 424/135.1 |

FOREIGN PATENT DOCUMENTS

| | | | | |
|---|---|---|---|---|
| WO | 99/50418 | * | 10/1999 | C12N 15/31 |
| WO | 01/07648 | * | 2/2001 | C12Q 1/68 |
| WO | WO2004090543 | | 10/2004 | |
| WO | 2009/095258 | * | 8/2009 | C12Q 1/04 |

OTHER PUBLICATIONS

Pucci et al, Journal of Bacteriology, Jan. 2002, p. 588-591, vol. 184(2), Direct quantiation of the numbers of individual penicillin binding proteins per cell in *Staphylococcus aureus*.*

Yan et al, The Journal of Infectious Diseases, vol. 170(3), Sep. 1994, pp. 609-614, Persistent Acylation of High-Molecular Weight Penicillin Binding Proteins by Penicillin Induces the Post antibiotic Effect in *Streptococcus pyogenes*.*

Chambers, HF et al, Binding of beta-lactam antibiotics to penicillin binding proteins in methicillin-resistant *Staphylococcus aureus*, 1990, vol. 161, pp. 1170-1176.*

(Continued)

*Primary Examiner* — Albert Navarro
*Assistant Examiner* — Ginny Portner

(57) ABSTRACT

The present invention relates to methods and systems for determining the antibiotic-resistance status of microorganisms. The invention further provides methods for determining the antibiotic-resistance status of microorganisms in situ within a single system.

31 Claims, 4 Drawing Sheets

(56) References Cited

OTHER PUBLICATIONS

Cohen, et al.; Cross-Resistance to Fluoroquinolones in Multiple-Antibiotic-Resistant (Mar) *Escherichia coli* Selected by Tetracycline or Chloramphenicol: Decreased Drug Accumulation Associated with Membrane Changes in Addition to OmpF Reduction; Anti. Agents and Chemo., (1989) vol. 33, No. 8, pp. 1318-1325.
de Lencastre, et al.; Molecular aspects of methicillin resistance in *Staphylococcus aureus*; J. Antimicrob. Chemother., (1994) vol. 33(1), pp. 7-24.
Eisinger et al.; Front-Face Fluorometry of Liquid Samples; Analytical Biochemistry (1979) vol. 94, pp. 15-21.
Galleni, et al.; A new, highyl Sensitive method for the detection and quantification of penicillin-binding proteins; Biochem. J., (1993) vol. 291, pp. 19-21.
Gee et al.; Fluorescent Bocillins: synthesis and application in the detection of penicillin-binding proteins; Elextrophoresis, (2001) 22(5), pp. 960-965.
Jarzembowski, et al.; Flow Cytometry as a Rapid Test for Detection of Penicillin Resistance Directly in Bacterial Cells in *Enterococcus faecalis* and *Staphylococcus aureus*; Curr. Microbiol., (2008) vol. 57, pp. 167-169.
Jarzembowski, et al.; Heterogeneity of Methicillin-Resistant *Staphylococcus aureus* Strains (MRSA) Characterized by Flow Cytometry; Curr. Microbiol. (2009) vol. 59, pp. 78-80.
Jarzembowski, et al.; Flow Cytometry Approach Study of *Enterococcus faecalis* Vancomycin Resistance by Detection of Vancomycin@FL Binding to the Bacterial Cells; Curr. Microbiol. (2010) vol. 57, pp. 167-169.
Kashket, et al.; Effects of Potassium Ions on the Electrical and pH Gradients Across the Membrane of *Streptococcus lactis* Cells; J. Bact. (1977) vol. 130, No. 3, pp. 1017-1023.
Lakaye, et al.; Synthesis, purification and kinetic properties of fluorescein-labelled penicillins; Biochem. J. (1994) vol. 300, pp. 141-145.
Li, et al.; Role of Efflux Pump(s) in Intrinsic Resistance of *Pseudomonas aeruginosa*: Resistance to Tetracycline, Chloramphenicol and Norfloxacin; Anti. Agents and Chemo.(1994) vol. 38, No. 8, pp. 1732-1741.
Moore, et al.; Interaction of Polycationic Antibiotics with *Pseudomonas aeruginosa* Lipopolysaccharide and Lipid A Studies by Using Dansyl-Polymyxin; Anti. Agents and Chemo. (1986) vol. 29, No. 3, pp. 496-500.
Morikawa, et al.; In vitro activities of piperacillin against beta-lactamase-negative ampicillin-resistant *Haemophilus influenzae*; Antimicrob. Agents and Chemother. (2004) vol. 48, No. 4, pp. 1229-1234.
Roychoudhury, et al.; Purification, properties, and kinetics of enzymatic acylation with beta-lactams of soluble penicillin-binding protein 2a; J. Biol. Chem.(1994) vol. 269, No. 16, pp. 12067-12073.
Russell et al.; Concentration of Ammonia Across Cell Membrane of Mixed Rumen Bacteria; J. Dairy Sci. (1987) vol. 70 pp. 970-976.
Utsui, et al.; Role of an Altered Penicillin-Binding Protein in Methicillin- and Cephem-Resistant *Staphylococcus aureus*; Anti. Agents and Chemo.(1985) vol. 28, No. 3, pp. 397-403.
Williams, et al.; Accumulation of Norfloxacin by *Mycobacterium aurum* and *Mycobacterium smegmatis*; Anti. Agents and Chemo. (1998) vol. 42, No. 4.
Zhao, et al.; Bocillin FL, a Sensitive and Commercially Available Reagent for Detection of Penicillin-Binding Proteins; Anti. Agents and Chemo. (1999) vol. 43, No. 5, pp. 1124-1128.
International Search Report and Written Opinion of the International Searching Authority for PCT/US2010/033879 dated Jul. 5, 2010.

* cited by examiner

METHODS FOR ANTIMICROBIAL
RESISTANCE DETERMINATION

CROSS REFERENCE TO RELATED APPLICATION

This application claims the benefit of U.S. Provisional Patent Application No. 61/215,594, entitled, "Methods for Antimicrobial Resistance Determination", filed May 7, 2009, which is incorporated herein.

FIELD OF THE INVENTION

The present invention relates to methods and systems for determining the antibiotic-resistance status of microorganisms. The invention further provides methods for determining the antibiotic-resistance status of microorganisms in situ within a single system.

BACKGROUND OF THE INVENTION

Bloodstream infections are associated with high morbidity and mortality, yet current diagnostic methods of culture, followed by biochemical identification and antibiotic susceptibility testing, can take several days to perform. Typically, empiric therapy is initiated based on clinical symptoms, and test results only impact clinical decisions when the initial therapy fails. The ability to characterize bloodstream infections within the first hour after a positive blood culture result would significantly boost the clinical relevance of the diagnostic information provided. Molecular amplification methods have been proposed to fill this need, but serious challenges to this approach remain. The positive blood culture broth itself represents a naturally amplified population of microorganisms with potential for use in a variety of rapid identification (ID) tests.

Methicillin-resistant *Staphylococcus aureus* (MRSA) is a dangerous community- and hospital-acquired pathogen that can rapidly cause infection even in healthy patients. It is also commonly present as normal flora on a number of elderly and sick patients, and has the ability to quickly cross-infect multiple patients in a health care environment. The mechanism of "methicillin resistance" is substantially mediated by the production of an altered penicillin binding protein 2, known as PBP2a, which retains functional enzymatic activity but has a significantly reduced affinity for beta-lactam antibiotics. Vancomycin-resistant enterococci (VRE) is another dangerous group of pathogens requiring immediate identification. In a manner similar to methicillin resistance, vancomycin resistance is also mediated by a reduced affinity of the antibiotic to it's cell membrane target.

Current methods to identify MRSA and VRE are labor-intensive and potentially unsafe due to steps that can result in aerosol exposure to the user. Rapid, yet safe and reliable methods are urgently needed to isolate microorganisms contained in blood culture broth that are compatible with rapid determination of resistance. Such methods are provided by the present invention.

SUMMARY OF THE INVENTION

The present invention provides methods for determining the antibiotic-resistance status of microorganisms. The methods allow determination of the antibiotic-resistance status of microorganisms more quickly than prior techniques, resulting in faster diagnoses (e.g., in a subject having or suspected of having septicemia and/or other infections) and characterization of contaminated materials (e.g., foodstuffs, water supplies, and pharmaceuticals). The steps involved in the methods of the invention, from obtaining a sample to the determination of the antibiotic-resistance status of microorganisms, can be carried out in a very short time frame to produce clinically relevant actionable information, e.g., in less than about 240 minutes. Additionally, the methods of the invention can be fully automated, thereby reducing the risk of handling infectious materials and/or contaminating the samples.

A first aspect of the invention relates to methods of determining the antibiotic-resistance status of a microorganism, comprising:
(a) contacting the microorganism with a resistance-determining affinity ligand under conditions whereby a microorganism/resistance-determining affinity ligand complex can be formed;
(b) separating microorganism/resistance-determining affinity ligand complex formed in (a) from unbound resistance-determining affinity ligand;
(c) determining the amount of resistance-determining affinity ligand bound to the microorganism in the microorganism/resistance-determining affinity ligand complex; and
(d) comparing the amount of resistance-determining affinity ligand bound to the microorganism in the microorganism/resistance-determining affinity ligand complex to the amount of resistance-determining affinity ligand bound by a known antibiotic-sensitive or antibiotic-resistant strain of the same microorganism or a population of known antibiotic-sensitive or antibiotic-resistant strains;
wherein if the microorganism in the microorganism/resistance-determining affinity ligand complex binds a different amount of resistance-determining affinity ligand than is bound by the antibiotic-sensitive microorganism or the microorganism in the microorganism/resistance-determining affinity ligand complex binds the same amount of resistance-determining affinity ligand as is bound by the antibiotic-resistant microorganism, the microorganism is identified as antibiotic-resistant.

In another aspect, the invention relates to a method for determining the antibiotic-resistance status of a microorganism, comprising:
(a) obtaining a test sample known to contain or that may contain microorganisms;
(b) contacting the microorganism in the test sample with a resistance-determining affinity ligand under conditions whereby a microorganism/resistance-determining affinity ligand complex can be formed;
(c) optionally adding one or more fluorescent dyes that measure cell metabolism or membrane integrity;
(d) optionally selectively lysing any non-microbial cells that may be present in the sample to produce a lysed sample;
(e) separating the microorganisms from other components of said test sample, or said lysed sample, to form a pellet of microorganisms;
(f) interrogating the pellet to produce measurements of the microorganism;
(g) determining the antibiotic-resistance status of the microorganisms in the test sample based by comparison of the measurements with measurements taken, or predicted, for antibiotic-resistant and/or antibiotic-susceptible microorganisms of the same species.

In one embodiment, the separating step is carried out by layering the microorganism/resistance-determining affinity ligand complex over a density cushion in a container (e.g., a hermetically sealed container) and centrifuging the container to pellet the microorganism/resistance-determining affinity ligand complex while the medium containing unbound ligand remains on top of the density cushion. In another embodiment, the container has an optical window at the bottom and/or sides so that the microorganism/resistance-determining affinity ligand complex pellet can be interrogated spectroscopically for the determining step. The antibiotic resistance state of the microorganisms can be determined by comparing the spectrum of the pellet to a spectrum or spectra of microorganisms of known antibiotic-resistance status. The ability to determine the antibiotic-resistance status of microorganisms directly in the pellet and/or in a hermetically sealed container without further handling enhances the safety of microbial identification.

In one embodiment, the determining step is carried out by recovering the microorganism/resistance-determining affinity ligand complex pellet, resuspending the microorganisms in a suitable medium and interrogating the resuspended microorganisms, e.g., spectroscopically. In another embodiment, the methods further comprise performing further identification and/or characterization tests (e.g., drug resistance, virulence factors, antibiogram) on the resuspended microorganisms.

In a further aspect, the invention relates to systems for determining the antibiotic-resistance status of a microorganism, comprising:
(a) a container comprising a microorganism or a sample containing the microorganism and a resistance-determining affinity ligand;
(b) a density cushion; and
(c) a spectrometer to provide a measurement;
wherein said measurement determines the antibiotic-resistance status of a microorganism that has been concentrated in said container by an in situ separation within said system. In another embodiment, the system comprises a centrifuge for separating the microorganism from unbound resistance-determining affinity ligand.

The present invention is explained in greater detail in the figures herein and the description set forth below.

DETAILED DESCRIPTION OF THE INVENTION

Figure 1:
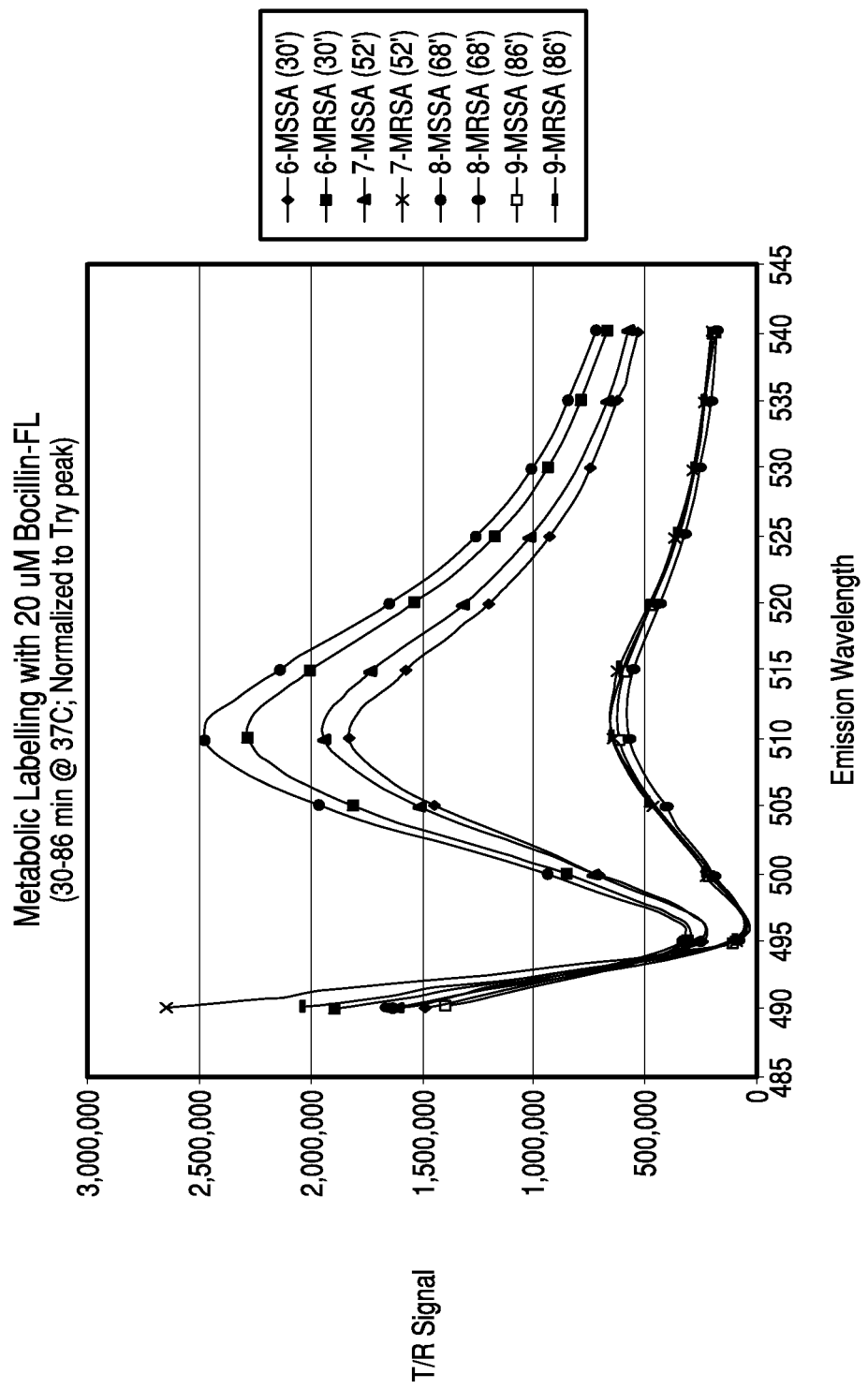
FIG. 1 shows metabolic labeling of methicillin-sensitive (MSSA) and -resistant (MRSA) *S. aureus* strains with BOCILLINT™-FL (BODIPY FL-labeled penicillin).

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Definitions.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the term "microorganism" is intended to encompass organisms that are generally unicellular, which can be multiplied and handled in the laboratory, including but not limited to, Gram-positive bacteria, Gram-negative bacteria, yeasts, molds, parasites, and mollicutes in any combination. Non-limiting examples of Gram-negative bacteria of this invention include bacteria of the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Stenotrophomonas, Brevundimonas, Ralstonia, Achromobacter, Fusobacterium, Prevotella, Branhamella, Neisseria, Burkholderia, Citrobacter, Hafnia, Edwardsiella, Aeromonas, Moraxella, Brucella, Pasteurella, Providencia,* and *Legionella*. Non-limiting examples of Gram-positive bacteria of this invention include bacteria of the following genera: *Enterococcus, Streptococcus, Staphylococcus, Bacillus, Paenibacillus, Lactobacillus, Listeria, Peptostreptococcus, Propionibacterium, Clostridium, Bacteroides, Gardnerella, Kocuria, Lactococcus, Leuconostoc, Micrococcus, Mycobacteria* and *Corynebacteria*. Non-limiting examples of yeasts and molds of this invention include those of the following genera: *Candida, Cryptococcus, Nocardia, Penicillium, Alternaria, Rhodotorula, Aspergillus, Fusarium, Saccharomyces* and *Trichosporon*. Non-limiting examples of parasites of this invention include those of the following genera: *Trypanosoma, Babesia, Leishmania, Plasmodium, Wucheria, Brugia, Onchocerca,* and *Naegleria*. Non-limiting examples of mollicutes of this invention include those of the following genera: *Mycoplasma* and *Ureaplasma*.

As used herein, the term "separate" is intended to encompass any sample of microorganisms that has been removed, concentrated or otherwise set apart from its original state, or from a growth or culture medium. For example, in accordance with this invention, microorganisms may be separated away (e.g., as a separated sample) from non-microorganisms or non-microorganism components that may otherwise interfere with characterization and/or identification. The term may include a layer of microorganisms sandwiched between two other layers, e.g., microorganisms collected on top of a high-density cushion after centrifugation, or a layer of microorganisms collected on a solid surface (e.g., a filter membrane). The term may also include a collection of microorganisms that has passed partially through a layer (e.g., a density cushion). As such, a separated microorganism sample may include any collection or layer of microorganisms and/or components thereof that is more concentrated than, or otherwise set apart from, the original sample, and can range from a closely packed dense clump of microorganisms to a diffuse layer of microorganisms. Microorganism components that can be comprised in a separated form or sample include, without limitation, pilli, flagella, fimbriae, and capsules in any combination. Non-microorganism components that are separated away from the microorganisms may include non-microorganism cells (e.g., blood cells and/or other tissue cells) and/or any components thereof.

As used herein, the term "pellet" is intended to encompass any sample of microorganisms that has been compressed or deposited into a mass of microorganisms. For example, microorganisms from a sample can be compressed or deposited into a mass at the bottom of a tube by centrifugation, or other known methods in the art. The term includes a collection of microorganisms (and/or components thereof) on the bottom and/or sides of a container following centrifugation. Microorganism components that can be comprised in a pellet include, without limitation, pilli, flagella, fimbriae, and capsules in any combination. In accordance with this invention, microorganisms may be pelleted away (e.g., as a substantially purified microorganism pellet) from non-microorganisms or non-microorganism components that may otherwise interfere with characterization and/or identification. Non-microorganism components that are separated away from the microorganisms may include non-microorganism cells (e.g., blood cells and/or other tissue cells) and/or any components thereof.

As used herein, the term "density cushion" refers to a solution having a homogenous density throughout.

As used herein, the term "resistance-determining affinity ligand" refers to any detectable compound or molecule that binds to an antibiotic-resistant microorganism to a different extent (e.g., in the amount of ligand bound, degree of binding, and/or affinity of binding, etc.) than an antibiotic-sensitive strain of the same microorganism. As used herein, the term includes unlabelled ligands and ligands that have been conjugated to a detectable label. In some embodiments, the resistance-determining affinity ligand binds to a lesser extent to the antibiotic-resistant strain compared to the antibiotic-sensitive strain. In other embodiments, the resistance-determining affinity ligand binds to a greater extent to the antibiotic-resistant strain compared to the antibiotic-sensitive strain.

As used herein, the term "bound," as applied to the resistance-determining affinity ligand, refers to physical association of the ligand with the microorganism. The term includes actual physical binding of the ligand to the microorganism, e.g., covalent or non-covalent binding to a structure of the microorganism (such as an intracellular or surface protein, nucleic acid, organelle, cell membrane, cell wall, etc.). The term also includes association of the ligand with the microorganism that does not involve physical binding, e.g., trapping of the ligand inside the microorganism. For example, the resistance-determining affinity ligand can comprise an enzyme substrate for an intracellular enzyme and the ligand becomes trapped inside the cell after it is acted on by the enzyme.

As used herein, the term "same microorganism" refers to a microorganism which is the same genus and species as the microorganism of interest.

As used herein, the term "binds a different amount," "difference in the amount of ligand bound," and variants thereof, refers to a difference in the amount of binding of resistance-determining affinity ligand between two microorganisms that is statistically significant. A "statistically significant" difference in binding is at least about 5%, e.g., at least about 10%, 20%, 30%, 40%, 50%, 60%, 70%, 80%, 90%, 100%, 150%, 200%, or more. The term "binds the same amount," and variants thereof, refers to a difference in the amount of binding of resistance-determining affinity ligand between two microorganisms that is less than about 20%, e.g., less than about 15%, 10%, 5%, 1%, or less. The amount of ligand bound can be determined by any method known to those of skill in the art, e.g., by measurement of an inherent property of the ligand or a property of a detectable label linked to the ligand.

As used herein, the term "a different binding affinity," "difference in the binding affinity of the ligand," and variants thereof, refers to a difference in the binding affinity of resistance-determining affinity ligand between two microorganisms that is at least about 5%, e.g., at least about 10%, 20%, 30%, 40%, 50%, 60%, 70%, 80%, 90%, 100%, 150%, 200%, or more. The term "the same binding affinity," and variants thereof, refers to a difference in the binding affinity of resistance-determining affinity ligand between two microorganisms that is less than about 20%, e.g., less than about 15%, 10%, 5%, 1%, or less. The binding affinity of a ligand can be determined by any method known to those of skill in the art, e.g., by measurement of an inherent property of the ligand or a property of a detectable label linked to the ligand.

The present invention provides methods for determining the antibiotic-resistance status of a microorganism. The rapid methods allow the determination of the antibiotic-resistance status of microorganisms more quickly than prior techniques, resulting in faster diagnoses (e.g., in a subject having or suspected of having septicemia and/or other infections) and characterization of contaminated materials (e.g., foodstuffs, water supplies, and pharmaceuticals). The steps involved in the methods of the invention, from obtaining a sample to determination of the antibiotic-resistance status of microorganisms, can be carried in a very short time frame to obtain clinically relevant actionable information. In certain embodiments, the methods of the invention can be carried out in less than about 240 minutes, e.g., in less than about 180, 120, 110, 100, 90, 80, 70, 60, 50, 40, 30, 20, 15, 10, 5, 4, 3, 2, or 1 minute. The tremendous rapidity of the methods of the invention represents an improvement over prior methods. The methods can be used to determine the antibiotic-resistance status of any microorganism as described herein. In one embodiment, the microorganism is a bacterium. In another embodiment, the microorganism is a yeast. In another embodiment, the microorganism is a mold. In a further embodiment, the microorganism is a parasite. In another embodiment, the microorganism is a mollicute. Additionally, the methods of the invention can be partially or fully automated, thereby reducing the risk of handling infectious materials and/or contaminating the samples.

A first aspect of the invention relates to methods of determining the antibiotic-resistance status of a microorganism, comprising:
(a) contacting the microorganism with a resistance-determining affinity ligand under conditions whereby a microorganism/resistance-determining affinity ligand complex can be formed;
(b) separating microorganism/resistance-determining affinity ligand complex formed in (a) from unbound resistance-determining affinity ligand;
(c) determining the amount of resistance-determining affinity ligand bound to the microorganism in the microorganism/resistance-determining affinity ligand complex; and
(d) comparing the amount of resistance-determining affinity ligand bound to the microorganism in the microorganism/resistance-determining affinity ligand complex to the amount of resistance-determining affinity ligand bound by a known antibiotic-sensitive or antibiotic-resistant strain of the same microorganism or a population of known antibiotic-sensitive or antibiotic-resistant strains;

wherein if the microorganism in the microorganism/resistance-determining affinity ligand complex binds a different amount of resistance-determining affinity ligand than is bound by the antibiotic-sensitive microorganism or the microorganism in the microorganism/resistance-determining affinity ligand complex binds the same amount of resistance-determining affinity ligand as is bound by the antibiotic-resistant microorganism, the microorganism is identified as antibiotic-resistant.

In another aspect, the invention relates to a method for determining the antibiotic-resistance status of a microorganism, comprising:
(a) obtaining a test sample known to contain or that may contain microorganisms;
(b) contacting the microorganism in the test sample with a resistance-determining affinity ligand under conditions whereby a microorganism/resistance-determining affinity ligand complex can be formed;
(c) optionally adding one or more fluorescent dyes that measure cell metabolism or membrane integrity;
(d) optionally selectively lysing any non-microbial cells that may be present in the sample to produce a lysed sample;
(e) separating the microorganisms from other components of said test sample, or said lysed sample, to form a pellet of microorganisms;
(f) interrogating the pellet to produce measurements of the microorganism;
(g) determining the antibiotic-resistance status of the microorganisms in the test sample based by comparison of the measurements with measurements taken, or predicted, for antibiotic-resistant and/or antibiotic-susceptible microorganisms of the same species.

One advantage of the methods of the present invention is the rapidity with which the methods can be carried out. Another advantage is that the methods can be carried out on intact microorganisms. Identification of antibiotic-resistant microorganisms can be made without the need to lyse or otherwise destroy the microorganism in order to, e.g., expose intracellular components or to isolate cell membranes, although the methods described herein can also be carried out with lysed or otherwise non-intact microorganisms. Thus, there is no requirement for harsh conditions, such as extreme pH, detergent, or heat. Additionally, because the microorganisms need not be destroyed by the determination methods, they can remain available for further tests or uses.

Samples

In some embodiments of the invention, the microorganism to be tested for antibiotic resistance is present in one or more samples. Samples that may be tested by the methods of the invention include both clinical and non-clinical samples in which microorganism presence and/or growth is or may be suspected, as well as samples of materials that are routinely or occasionally tested for the presence of microorganisms. The amount of sample utilized may vary greatly due to the versatility and/or sensitivity of the method. Sample preparation can be carried out by any number of techniques known to those skilled in the art although one of the advantages of the present invention is that complex sample types, such as, e.g., blood, bodily fluids, and/or other opaque substances, may be tested directly utilizing the system with little or no extensive pretreatment.

Clinical samples that may be tested include any type of sample typically tested in clinical or research laboratories, including, but not limited to, blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, other body fluids, and the like.

The present invention finds use in research as well as veterinary and medical applications. Suitable subjects from which clinical samples can be obtained are generally mammalian subjects, but can be any animal. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects. Subjects from which samples can be obtained include, without limitation, mammals, birds, reptiles, amphibians, and fish.

Non-clinical samples that may be tested also include substances, encompassing, but not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, fruit), blood products (e.g., platelets, serum, plasma, white blood cell fractions, etc.), donor organ or tissue samples, biowarfare samples, and the like. The method is also particularly well suited for real-time testing to monitor contamination levels, process control, quality control, and the like in industrial, commercial, and/or clinical settings.

In one embodiment of the invention, samples are obtained from a subject (e.g., a patient) having or suspected of having a microbial infection. In one embodiment, the subject has or is suspected of having septicemia, e.g., bacteremia or fungemia. The sample may be a blood sample directly from the subject. The sample may be from a blood culture grown from a sample of the patient's blood, e.g., a BacT/ALERT® blood culture. The blood culture sample may be from a positive blood culture, e.g., a blood culture that indicates the presence of a microorganism. In certain embodiments, the sample is taken from a positive blood culture within a short time after it turns positive, e.g., within about 6 hours, e.g., within about 5, 4, 3, or 2 hours, or within about 60 minutes, e.g., about 55, 50, 45, 40, 35, 30, 25, 20, 15, 10, 5, 4, 3, 2, or 1 minute. In one embodiment, the sample is taken from a culture in which the microorganisms are in log phase growth. In another embodiment, the sample is taken from a culture in which the microorganisms are in a stationary phase.

The present invention provides high sensitivity for the detection of antibiotic-resistant microorganisms. This enables detection without first having to go through the steps of isolating microorganisms by growing them on a solid or semi-solid medium, and sampling the colonies that grow. However, in one embodiment of the invention, the sample is from a microbial (e.g., bacteria, yeast, or mold) colony grown on a solid or semisolid surface.

The volume of the sample should be sufficiently large to produce a detectable amount (e.g., a pellet) of microorganisms which can be interrogated after the separation step of the methods of the invention is carried out. Appropriate volumes will depend on the source of the sample and the anticipated level of microorganisms in the sample. For example, a positive blood culture will contain a higher level of microorganisms per volume than a drinking water sample to be tested for contamination, so a smaller volume of blood culture medium will be needed as compared to the drinking water sample. In general, the sample size can be less than about 50 ml, e.g., less than about 40, 30, 20, 15, 10, 5, 4, 3, or 2 ml. In certain embodiments, the sample size can be about 1 ml, e.g., about 0.75, 0.5, or 0.25 ml. In certain embodiments in which the separation is carried out on a microscale, the sample size can be less than about 200 µl, e.g., less than about 150, 100, 50, 25, 20, 15, 10, or 5 µl. In some embodiments (e.g., when the sample is expected to comprise a small number of microorganisms), the sample size can be about 100 ml or more, e.g., about 250, 500, 750, or 1000 ml or more.

Contact Step

In one aspect of the invention, the microorganism or a sample containing the microorganism is contacted with a resistance-determining affinity ligand. In one embodiment, the contact can occur in the sample medium, e.g., by adding ligand to the sample. In another embodiment, the contact occurs in a binding mixture or composition into which both the microorganism and the ligand are introduced. In a further embodiment, the resistance-determining affinity ligand is contained within the density cushion in the separation container. In one embodiment, the resistance-determining affinity ligand is an antibiotic, e.g., penicillin or another β-lactam antibiotic, vancomycin or other glycopeptide antibiotic, polymyxin B, or ceftobiprole as well as any combination thereof. In another embodiment, the resistance-determining affinity ligand is a monoclonal or polyclonal antibody or antibody fragment, nucleic acid probe, aptamer, ligand, enzyme substrate, peptide mimetic, phage-derived binding protein, lipid, carbohydrate, polysaccharide, or protein, or any combination thereof. If the resistance-determining affinity ligand does not itself give out a detectable signal, the ligand can be labeled to provide a detectable signal, such as by conjugating the ligand to a marker (e.g., visible or fluorescent). Markers include, without limitation, fluorescent, luminescent, phosphorescent, radioactive, Raman-active, mass spectrometry-reactive and/or colorimetric compounds. Labeled resistance-determining affinity ligands can include, without limitation, labeled penicillin (e.g., BOCILLIN FL penicillin) and labeled vancomycin (e.g., BODIPY FL vancomycin) (Life Technologies, Carlsbad, Calif.).

The contacting of the resistance-determining affinity ligand and the microorganism or a sample containing the microorganism can be carried out by any method as long as a detectable amount of binding occurs between the ligand and the microorganism (e.g., a microorganism/resistance-determining affinity ligand complex is formed) and there is a measurable difference in the amount of binding or the binding affinity to antibiotic-sensitive and antibiotic-resistant microorganisms. The amount of resistance-determining affinity ligand placed in contact with the microorganism and the length of time of contact are sufficient for binding of the ligand to the microorganism to occur resulting in formation of a microorganism/resistance-determining affinity ligand complex, and will depend on several factors, including the type of microorganism, type of ligand, affinity of the ligand for the microorganism, whether the binding target for the ligand is extracellular or intracellular, temperature, buffer conditions, etc., as would be well known to one of skill in the art. The contact time can be, for example, about 240 minutes or less, e.g., about 180, 120, 90, 60, 50, 40, 30, 20, 10, 10, 5, 4, 3, 2, 1 minute or less. The contacting can take place at any temperature suitable for binding of the ligand to the microorganism to occur, e.g., about 4° C. to about 50° C., e.g., about 15° C. to about 40° C., e.g., about 37° C. or about room temperature. The contacting step can be carried out in a suitable container, e.g., in the same container in which the separation step is carried out or in a separate container.

Separation Step

After the microorganism or sample containing the microorganism has been contacted with a resistance-determining affinity ligand and a detectable or measurable amount of binding of the ligand to the microorganism has occurred, a separation step can be carried out to separate the microorganism/resistance-determining affinity ligand complex from unbound resistance-determining affinity ligand as well as to separate the microorganism from other components of the sample and/or binding mixture or composition. In one embodiment, the separation step concentrates the microorganism/resistance-determining affinity ligand complexes into a pellet that can be interrogated for determination of the antibiotic-resistance status of the microorganism. The separation of the microorganism from other components of the sample and/or binding mixture or composition does not have to be complete, i.e., it is not required that 100% separation occur. All that is required is that the separation of the microorganism from other components (e.g., unbound ligand) be sufficient to permit interrogation of the microorganism without substantial interference from the other components. For example, the separation can result in a microorganism pellet that is at least about 10, 20, 30, 40, 50, 60, 70, 80, 90, 95, 96, 97, 98, or 99% pure or higher.

In one embodiment, the separation is carried out by a centrifugation step in which the microorganism/resistance-determining affinity ligand complexes are placed on top of a density cushion in a separation container and the container is centrifuged under conditions in which the complexes pellet at the bottom and/or sides of the container and the unbound ligand and other components of the sample and/or binding mixture or composition stay on top of the density cushion or within the top portion of the density cushion. This separation isolates the microorganisms away from materials, such as medium, cell debris, and/or other components that might interfere with detecting and/or measuring the binding of resistance-determining affinity ligand to the microorganisms. In one embodiment, the density cushion also serves to separate live microorganisms from dead microorganisms (which do not pass completely through the density cushion). In another embodiment, the density cushion does not comprise a density gradient, either before or after the centrifugation. In other words, the separation container is not centrifuged for a sufficient amount of time and/or acceleration for the material making up the density cushion to form a density gradient.

The density of the cushion is selected such that the microorganism/resistance-determining affinity ligand complexes in the sample and/or binding mixture or composition pass through the cushion while unbound resistance-determining affinity ligand and other components of the sample and/or binding mixture or composition (e.g., blood culture broth, cell debris) remain on top of the cushion or do not pass all of the way through the density cushion. The density may also be selected to separate live microorganisms (which pass through the cushion) from dead microorganisms (which do not pass through the cushion). Suitable densities will depend on the material used in the density cushion and on the sample to be separated. In one embodiment, the density of the cushion is in the range of about 1.025 to about 1.120 g/ml, e.g., about 1.030 to about 1.070 g/ml, about 1.040 to about 1.060 g/ml or any range between about 1.025 to about 1.120 g/ml. In another embodiment, the density of the cushion is about 1.025, 1.030, 1.035, 1.040, 1.045, 1.050, 1.055, 1.060, 1.065, 1.070, 1.075, 1.080, 1.085, 1.090, 1.095, 1.100, 1.105, 1.110, 1.115, or 1.120 g/ml.

The material for the density cushion can be any material or combination of materials that has the appropriate density range for the methods of the invention. Suitable materials that can be used to prepare the density cushion include low viscosity, high density oils, such as microscope immersion oil (e.g., Type DF; Cargille Labs, New York) and mineral oil (e.g., Drakeol® 5, Draketex 50, Peneteck®; Penreco Co., Pennsylvania). Another suitable material is colloidal silica.

The colloidal silica may be uncoated (e.g., Ludox® (W.R. Grace, CT)) or coated, e.g., with silane (e.g., PureSperm® (Nidacon Int'l, Sweden), Isolate® (Irvine Scientific, Santa Ana, Calif.) or Percoll™ Plus (Sigma-Aldrich, St. Louis, Mo.)) or polyvinylpyrrolidone (e.g., Percoll™ (Sigma-Aldrich, St. Louis, Mo.)). In one embodiment, the colloidal silica exhibiting the least interference with spectroscopic interrogation is selected, e.g., the material with the lowest intrinsic fluorescence. The colloidal silica may be diluted in any suitable medium to form the proper density, e.g., balanced salt solutions, physiological saline, and/or 0.25 M sucrose. Suitable densities can be obtained with colloidal silica at a concentration of about 15% to about 80% v/v, e.g., about 20% to about 65% v/v.

Another suitable material is an iodinated contrast agent (e.g., iohexol (Omnipaque™ NycoPrep™, or)Nycodenz®) and iodixanol (Visipaque™ or OptiPrep™). Suitable densities can be obtained with iohexol or iodixanol at a concentration of about 10% to about 25% w/v, e.g., about 14% to about 18% w/v, for blood culture samples. Sucrose can be used as a density cushion at a concentration of about 10% to about 30% w/v, e.g., about 15% to about 20% w/v, for blood culture samples. Other suitable materials for density cushions include, without limitation, silicone oil (polydimethylsiloxane), fluorosilicone oil, silicone gel, metrizoate-Ficoll® (LymphoPrep™), e.g., at a concentration of about 75% to about 100% for blood culture samples, diatrizoate-dextran (PolymorphoPrep™), e.g., at a concentration of about 25% to about 50% for blood culture samples, carboxymethyl cellulose, hydroxypropylmethyl cellulose, polyethylene oxide (high molecular weight), polyoxyalkylene ether (e.g., Pluronic® F127, Pluronic® F68), mixtures of Pluronic® compounds, polyacrylic acid, cross-linked polyvinyl alcohol, cross-linked polyvinyl pyrrolidine, PEG methyl ether methacrylate, pectin, agarose, xanthan, gellan, Phytagel® Gellan Gum (e.g., Phytagel™), sorbitol, a sucrose and epichlorohydrin copolymer (Ficoll® (e.g., Ficoll® 400 at a concentration of about 10% to about 15% for blood culture samples)), glycerol, dextran (e.g., at a concentration of about 10% to about 15% for blood culture samples), glycogen, cesium chloride (e.g., at a concentration of about 15% to about 35% for blood culture samples), perfluorocarbon fluids (e.g., perfluoro-n-octane), hydrofluorocarbon fluids (e.g., Vertrel XF), and the like as are well known in the art. The density cushion can also be made up of a combination of materials, including a combination of any two or more of the materials listed above. In one embodiment, the density cushion is made up of a combination of immersion oil and mineral oil, e.g., in a ratio of about 0.8 to about 1.2 parts immersion oil to about 0.7 to about 1.0 parts mineral oil. In one embodiment, the density cushion comprises DF immersion oil and Drakeol 5 mineral oil, e.g., 1.000 part type DF immersion oil:0.875 part Drakeol 5 mineral oil. In another embodiment, the density cushion consists of cesium chloride (e.g., 24% w/v cesium chloride).

The volume/height of the density cushion should be sufficient to achieve separation of the microorganism/resistance-determining affinity ligand complexes from unbound resistance-determining affinity ligand and other components of the sample and/or binding mixture or composition. The volume will depend on the size and shape of the separation container. In general, a volume of about 0.1 to about 5 ml can be used, e.g., about 0.2 to about 1 ml, e.g., about 0.2 ml to about 0.5 ml. If the separation is performed on a microscale, the volume of the density cushion can be about 1 µl to about 100 µl, e.g., about 5 µl to about 50 µl. The volume of sample and/or binding mixture or composition laid or layered on top of the density cushion should be sufficient to provide enough microorganisms to be detectable and/or measurable, e.g., to produce a pellet suitable for interrogation. In general, any volume that fits into the container can be used. For example, a volume of about 0.1 ml to about 5 ml can be used, e.g., about 0.2 ml to about 1 ml, e.g., about 0.2 ml to about 0.5 ml. If the separation is performed on a microscale, the volume can be about 1 µl to about 100 µl, e.g., about 5 µl to about 50 µl. In certain embodiments, the volume can be reduced and/or the concentration of microorganisms increased prior to placing the sample and/or binding mixture or composition in the separation container so that the sample and/or binding mixture or composition is of an appropriate volume to fit into the container. For example, the sample and/or binding mixture or composition can be filtered to reduce the volume and/or to collect the microorganisms. The available space in the container for sample and/or binding mixture or composition will depend on the size and shape of the container. In some embodiments, an intermediate layer (liquid or solid) can be placed on top of the density cushion before the sample and/or binding mixture or composition is laid or layered on top in order to prevent any mixing of the density cushion and the sample and/or binding mixture or composition. In one embodiment, the intermediate layer can be polypropylene beads. In another embodiment, a small air bubble can be positioned between the density cushion and the sample and/or binding mixture or composition to prevent mixing. In a further embodiment, the density cushion can be layered on top of a high density material (e.g., a perfluorocarbon fluid) such that the microorganism/resistance-determining affinity ligand complexes pass through the density cushion during the separation and collect at the interface between the density cushion and the high density material.

In one embodiment of the invention, the separation container is centrifuged so that the microorganism/resistance-determining affinity ligand complexes form a pellet directly on the bottom of the container. The container is centrifuged at a sufficient acceleration and for a sufficient time for the microorganism/resistance-determining affinity ligand complexes to pellet and/or be separated from unbound ligand and other components of the sample and/or binding mixture or composition. The centrifugation acceleration can be about 1,000×g to about 20,000×g, e.g., about 2,500×g to about 15,000×g, e.g., about 7,500×g to about 12,500×g, etc. The centrifugation time can be about 30 seconds to about 30 minutes, e.g., about 1 minute to about 15 minutes, e.g., about 1 minute to about 5 minutes. The centrifugation can be carried out at a temperature of about 2° C. to about 45° C., e.g., about 15° C. to about 40° C., e.g., about 20° C. to about 30° C. In one embodiment, the separation container comprises a closure, and the closure is applied to the container to form a hermetic seal prior to centrifugation. The presence of a closure decreases the risks from handling microorganisms that are or may be infectious and/or hazardous, as well as the risk of contaminating the sample and/or binding mixture or composition. One of the advantages of the methods of the invention is the ability to carry out any one or more of the steps of the methods (e.g., contact, separation, detection, and/or comparison) with the microorganisms in a sealed container (e.g., a hermetically sealed container). The present methods, involving the use of automated systems, avoid the health and safety risks associated with handling of highly virulent microorganisms, such as occurs with recovery of microorganisms from samples for direct testing. In one embodiment, the container is not centrifuged for a sufficient time and/or force for a density gradient to form within the density cushion. The present invention does not involve ultracentrifugation, e.g., centrifugation at forces greater than about 100,000×g. Further, the present invention does not involve isopycnic (equilibrium) sedimentation or banding.

The separation container may be any container with sufficient volume to hold a density cushion and a sample and/or binding mixture or composition. In one embodiment, the container fits or can be fitted into a centrifuge rotor. The volume of the container can be about 0.1 ml to about 25 ml, e.g., about 1 ml to about 10 ml, e.g., about 2 ml to about 8 ml. If the separation is done on a microscale, the volume of the container can be about 2 µl to about 100 µl, e.g., about 5 µl to about 50 µl. In one embodiment, the container has a wide internal diameter in an upper portion to hold the sample and/or binding mixture or composition and the majority of the density cushion, and a more narrow internal diameter in a lower portion where the pellet of microorganism/resistance-determining affinity ligand complexes is collected. The narrow portion can have an internal diameter of about 0.04 to about 0.12 inches, e.g., about 0.06 to about 0.10 inches, e.g., about 0.08 inches. The wide portion can have an internal diameter of about 0.32 to about 0.40 inches, e.g., about 0.34 to about 0.38 inches, e.g., about 0.36 inches. For microscale separations, the internal diameters can be even smaller. For example, the internal diameter of the narrow portion can be about 0.001 to about 0.04 inches, e.g., about 0.002 to about 0.01 inches. A tapered internal diameter portion can connect the upper and lower portions. The tapered portion can have an angle of about 20 to about 70 degrees, e.g., about 30 to about 60 degrees. In one embodiment, the lower narrow portion is less than half of the total height of the container, e.g., less than about 40%, 30%, 20%, or 10% of the total height of the container. The container can have a closure device attached or may be threaded to accept a closure device (e.g., a cap) such that the container can be hermetically sealed during centrifugation. In certain embodiments, the container is designed such that the microorganism pellet can be readily recovered from the container after separation, either manually or in an automated manner (so that technicians are not exposed to the container contents). For example, the container can comprise a removable portion or a break-away portion which contains the pellet and which can be separated from the rest of the container. In another embodiment, the container comprises means for access to the pellet after separation, such as one or more ports or permeable surfaces for insertion of a syringe and/or other sampling device and/or for drawing off the pellet. In one embodiment, the container can be a tube, e.g., a centrifuge tube. In another embodiment, the container can be a chip or a card. In one embodiment, the container is a stand alone container, i.e., a device for separating a single sample. In other embodiments, the container is part of a device that comprises two or more separation containers such that multiple samples can be separated at the same time. In one embodiment, the device comprises 2, 3, 4, 5, 6, 7, 8, 9, 10, 12, 15, 20, 25, 30, 36, 42, 48, 60, 72, 84, 96, or more separation containers. In one embodiment, the separation container is the separation device disclosed in related U.S. patent application Ser. No. 12/589,969, entitled "Separation Device for Use in the Separation, Characterization and/or Identification of Microorganisms", filed Oct. 30, 2009.

The container can comprise an optical window through which the determination of binding (e.g., detection of an amount of binding and/or measurement of a binding affinity) can occur. The optical window may be on the bottom, top, and/or sides of the container. The window can be composed of any material that is transparent to light (e.g., at least a portion of the near infrared (NIR; 700 nm-1400 nm), ultraviolet (UV; 190 nm-400 nm) and/or visible (VIS; 400 nm-700 nm) light spectrum). Examples of suitable materials include, without limitation, acrylic, methacrylate, quartz, fused silica, sapphire, a cyclic olefin copolymer (COC), polystyrene, polycarbonate and/or polypropylene. In one embodiment, the entire container is made of optical window material. In another embodiment, the container may be prepared (e.g., molded) from two or more separate parts, such as an optical UV-VIS-NIR transparent component for the optical window and another material (e.g., a lower-cost standard molding plastic) to make up the rest of the container. In one embodiment, the optical window is thin enough to permit spectroscopic interrogation, which will depend on the material of the window. In another embodiment, the optical window is as thin as possible to reduce interference with spectroscopic interrogation. For example, the window can have a thickness of less than about 0.20 inches, e.g., less than about 0.15, 0.10, or 0.05 inches.

In another embodiment, the separation is carried out by a filtration step in which the sample and/or binding mixture or composition is placed in a device fitted with a selective filter or filter set with pore sizes that retain the microorganisms. The retained microorganisms may be washed by gently passing a suitable buffer through the filter. The washed microorganisms may then be interrogated directly on the filter and/or recovered for interrogation by directly sampling the surface of the filter or by back-flushing the filter with suitable aqueous buffer.

Optional Lysis Step

In some embodiments of the methods of the invention, the sample comprising the microorganism optionally can be treated to selectively lyse non-microbial cells (e.g., undesired cells) that may be present in the sample, e.g., blood cells and/or tissue cells, e.g., prior to the separation step. Cells are lysed to permit separation of microorganisms from other components of the sample. The separation of microorganisms from other components prevents interference during the detection step. If non-microorganism cells are not expected to be present or not likely to be present in the sample or not expected to interfere with the detection step, the lysis step need not be carried out. In one embodiment, the cells to be lysed are non-microorganism cells that are present in the sample and no microorganism cells that may be present in the sample are lysed. However, in some embodiments, the selective lysing of specific classes of microorganisms may be desirable and thus can be carried out according to the methods described herein and as are well known in the art. For example, a class of undesired microorganisms can be selectively lysed, e.g., yeast are lysed while bacteria are not or vice versa. In another embodiment, the desired microorganisms are lysed in order to separate a particular subcellular component of the microorganisms, e.g., cell membranes or organelles. In one embodiment, all of the non-microbial cells are lysed. In other embodiments, a portion of the non-microbial cells are lysed, e.g., enough cells to prevent interference with the detection step. The lysing of cells may be carried out by any method known in the art to be effective to selectively lyse cells with or without lysing microorganisms, including, without limitation, addition of a lysis solution, sonication, osmotic shock, freeze-thaw cycles, chemical treatment, and/or a combination thereof.

A lysis solution is one that is capable of lysing cells, e.g., non-microorganism cells (e.g., by solubilizing eukaryotic cell membranes) and/or microorganism cells. In one embodiment, the lysis solution can comprise one or more detergents, one or more enzymes, or a combination of one or more detergents and one or more enzymes, and can further include additional agents. In one embodiment, the detergent can be a non-denaturing lytic detergent, such as Triton® X-100 Triton® X-100-R, Triton® X-114, NP-40, Genapol C-100, Genapol X-100, Igepal® CA 630, Arlasolve™200, Brij® 96/97, CHAPS, octyl β-D-glucopyranoside, saponin, nonaethylene glycol monododecyl ether (C12E9, polidocenol), and polyoxyethylene ether (C12E10, e.g., Genapol® C-100). Optionally, denaturing lytic detergents can be included, such as sodium dodecyl sulfate, N-laurylsarcosine, sodium deoxycholate, bile salts, hexadecyltrimethylammonium bromide, SB3-10, SB3-12, amidosulfobetaine-14, and C7BzO. Optionally, solubilizers can also be included, such as Brij® 98, Brij® 58, Brij® 35, Tween® 80, Tween® 20, Pluronic® L64, Pluronic® P84, Pluronic® F108, non-detergent sulfobetaines (NDSB 201), amphipols (PMAL-C8), and methyl-β-cyclodextrin. Typically, non-denaturing detergents and solubilizers are used at concentrations above their critical micelle concentration (CMC), while denaturing detergents may be added at concentrations below their CMC. For example, non-denaturing lytic detergents can be used at a concentration of about 0.010% to about 10%, e.g., about 0.015% to about 1.0%, e.g., about 0.05% to about 0.5%, e.g., about 0.10% to about 0.30% (final concentration after dilution with the sample). In another embodiment, polyoxyethylene detergent detergents may be preferred. The polyoxyethylene detergent can comprise the structure $C_{12-18}/E_{9-10}$, wherein C12-18 denotes a carbon chain length of from 12 to 18 carbon atoms and E9-10 denotes from 9 to 10 oxyethylene hydrophilic head groups. For example, the polyoxyethylene detergent can be selected from the group consisting of Brij® 97, Brij® 96V, Genapol C-100, Genapol X-100, polidocenol, or a combination thereof. Enzymes that can be used in lysis solutions include, without limitation, enzymes that digest nucleic acids and other membrane-fouling materials (e.g., proteinase XXIII, DNase, neuraminidase, polysaccharidase, Glucanex®, and Pectinex®). Other additives that can be used include, without limitation, reducing agents such as 2-mercaptoethanol (2-Me) or dithiothreitol (DTT) and stabilizing agents such as magnesium, pyruvate, and humectants. The lysis solution can be buffered at any pH that is suitable to lyse the desired cells, and will depend on multiple factors, including without limitation, the type of sample, the cells to be lysed, and the detergent used. In some embodiments, the pH can be in a range from about 2 to about 13, e.g., about 6 to about 13, e.g., about 8 to about 13, e.g., about 10 to about 13. Suitable pH buffers include any buffer capable of maintaining a pH in the desired range, e.g., about 0.05 M to about 1.0 M CAPS.

In one embodiment, the sample and the lysis solution are mixed and then incubated for a sufficient time for lysis and solubilization of cell membranes to occur, e.g., about 1, 2, 3, 4, 5, 10, 15, 20, 25, 30, 40, 50, or 60 seconds, or about 2, 3, 4, 5, 6, 7, 8, 9, 10, 15, or 20 minutes or longer, e.g., about 1 second to about 20 minutes, about 1 second to about 5 minutes, or about 1 second to about 2 minutes. The incubation time will depend on the strength of the lysis solution, e.g., the concentration of the detergent and/or enzymes and the temperature of lysis. In general, milder lysis buffers will require more time and a greater dilution of the sample to fully solubilize non-microbial cells. The strength of the lysis solution can be selected based on the microorganisms known to be or suspected to be in the sample. For microorganisms that are more susceptible to lysis, a mild lysis solution can be used. The lysis can take place at a temperature of about 2° C. to about 45° C., e.g., about 15° C. to about 40° C., e.g., about 30° C. to about 40° C. In one embodiment, the lysis solution can be loaded into a syringe and the sample can then be aspirated into the syringe such that mixing and incubation occurs within the syringe.

In some embodiments, the lysis conditions (e.g., the solution or the incubation time), as well as the separation and/or interrogation steps, can be sufficient to kill some or all of the microorganisms in the sample. The methods of the present invention are highly versatile and do not require that the microorganisms be alive for the isolation and identification to occur. In certain embodiments, some or all of the microorganisms may be dead, with death occurring before, during, and/or after the steps of the methods being carried out.

Detection/Comparison Step

Once the microorganism/resistance-determining affinity ligand complex has been separated from unbound resistance-determining affinity ligand, the amount of resistance-determining affinity ligand bound to the microorganism or the binding affinity of the ligand can be detected and/or measured. If the microorganism/resistance-determining affinity ligand complex is separated by centrifugation to produce a pellet, the pellet can be interrogated to detect the amount bound or binding affinity of the resistance-determining affinity ligand. In one embodiment, the interrogation takes place in a non-invasive manner, that is, the pellet is interrogated while it remains in the separation container. In another embodiment, the separation container remains sealed throughout the interrogation. The ability to identify antibiotic-resistant microorganisms in a non-invasive manner, optionally coupled with keeping the container sealed throughout the separation and characterization process and automating some or all of the procedure avoids the constant handling of contaminated and/or infectious samples and greatly increases the safety of the entire process. Furthermore, the ability to characterize microorganisms by direct interrogation without further processing of the pellet (e.g., resuspension, plating, and growth of colonies), greatly increases the speed with which identification of antibiotic-resistant microorganisms can be made.

In certain aspects of the invention, the methods involve recovering the pellet of microorganism/resistance-determining affinity ligand complexes formed during the separation step or a portion thereof from the separation container prior to interrogation of the microorganisms. For example, after formation of the pellet, the fluids can be aspirated way from the pellet and the pellet resuspended in a suitable medium (e.g., a medium in which the microorganisms are viable). The resuspended microorganisms can be removed from the separation container. The microorganisms can then be interrogated for detection of ligand binding or affinity, e.g., in the suspension or after they have been repelleted. In other embodiments, the resuspended microorganisms can be interrogated in the separation container, e.g., in the suspension or after they have been repelleted. In another embodiment, the pellet is recovered and/or resuspended after in situ interrogation and further interrogation is then carried out. For example, techniques such as latex agglutination tests or automated phenotypic identification tests that can be applied to isolated microorganisms but not a pellet of microorganisms can be carried out on the recovered and/or resuspended microorganisms. In a further embodiment, microorganisms recovered from the pellet can be used directly for further interrogation (e.g., mass spectroscopy) without being resuspended.

In some embodiments, the pellet and/or the resuspended microorganisms can be interrogated spectroscopically. The spectroscopy can be used to analyze a property of the resistance-determining affinity ligand (e.g., an intrinsic property or a property of an attached label) in order to detect binding. In addition to detecting the resistance-determining affinity ligand, the spectroscopy can also be used to analyze one or more intrinsic properties (e.g., intrinsic fluorescence) of the microorganism in the complex, e.g., a property present within the microorganism in the absence of additional agents, such as stains, dyes, binding agents, etc. The intrinsic fluorescence or auto fluorescence of the microorganism, particularly bacteria, leverages the fact that the bacteria contain natural fluorophores (e.g., tryptophan, tyrosine, phenylalanine, NADH, and flavin) that can be excited via a multi-wavelength light source. In these embodiments, the binding of the resistance-determining affinity ligand can be compared to the intrinsic property signal of the microorganism and the amount of ligand bound can be calculated on a per cell basis. The interrogation can be carried using, for example, fluorescence spectroscopy, diffuse reflectance spectroscopy, adsorption and transmission spectroscopy, infrared spectroscopy, terahertz spectroscopy, Raman spectroscopy, including Surface Enhanced Raman Spectroscopy (SERS), spacially-offset Raman spectroscopy and/or resonance Raman spectroscopy. To enhance Raman (SERS) and fluorescence signals, microorganisms can either be coated with gold and/or silver nanoparticles prior to centrifugation, and/or the inner optical surface can be pre-coated with metal colloids of particular size and shape (Lakowicz, *Anal. Biochem.* 337:171 (2005) for fluorescence; Efrima et al., *J. Phys. Chem. B.* (*Letter*) 102: 5947 (1998) for SERS). In another embodiment, the nanoparticles are present in the density cushion prior to centrifugation and associate with microorganisms as the microorganisms pass through the density cushion. In other embodiments, the microorganisms (resuspended or in the pellet) can be interrogated using mass spectroscopy techniques, such as MALDI-TOF mass spectroscopy, DESI mass spectroscopy, GC mass spectroscopy, LC mass spectroscopy and Selected Ion Flow Tube (SIFT) spectroscopy. In one embodiment, the pellet is interrogated while it remains in the separation container. The container can be interrogated through an optical window in the container. The optical window may be on the bottom and/or any side or sides and/or on the top of the container. In one embodiment, the separation container fits into or can be fitted into a holder in a spectrometer in a suitable position for interrogation. The spectroscopic interrogation can be carried out by any technique known to those of skill in the art to be effective for detecting one or more intrinsic or extrinsic properties of resistance-determining affinity ligands and/or microorganisms. For example, front face fluorescence (where the exciting and emitted light enters and leaves the same optical surface, and if the sample is generally optically thick, the excitation light penetrates a very short distance into the sample (see, e.g., Eisinger, J., and J. Flores, "Front-face fluorometry of liquid samples," *Anal. Biochem.* 94:15 (1983)) can be used for detection of microorganisms in pellets. Other forms of measurement, such as epifluorescence, reflectance, absorbance, and/or scatter measurements, can also be employed in the present invention. In certain aspects of the invention, in addition to analyzing one or more intrinsic properties of the microorganism for the purposes of determining ligand binding on a per cell basis, the intrinsic properties can be used to identify the microorganism. In one embodiment, the intrinsic properties of the microorganism are compared to a database of intrinsic properties of known organisms in order to identify the microorganism.

In yet another embodiment, the determination of resistance can be made indirectly by measuring changes in measured properties (e.g., changes in intrinsic fluorescence properties) of the test microorganism and/or through the use of fluorescent dyes used to monitor metabolism or membrane integrity. In accordance with this embodiment, the ligand or agent itself does not need to give out a detectable signal or be labeled with a detectable signal, as resistance is determined by indirectly measuring changes in measurable properties (e.g., changes in intrinsic fluorescence properties) resulting from the binding of the ligand or agent to the test microorganism. For example, the binding and/or exposure of an unlabelled antibiotic may change, alter or otherwise weaken the cell wall of the microorganism. The microorganism can be interrogated (e.g., by spectroscopy as described elsewhere herein) and the changes in cell wall can be indirectly measured and compared to a database of known resistant and/or sensitive microorganisms to determine antimicrobial-resistance status of the microorganism. Alternatively, the altered or otherwise weakened cell wall may be permeable (or more permeable) to one or more fluorescent dyes, accordingly, one or more fluorescent dyes may be added to the sample and the sample interrogated to detect and/or measure the fluorescent dyes to indirectly determine antimicrobial-resistance status of the microorganism (see, e.g., Example 5).

The sample illumination source, or excitation source, may be selected from any number of suitable light sources as known to those skilled in the art. Any portion of the electromagnetic spectrum that produces usable data can be used. Light sources capable of emission in the ultraviolet, visible and/or near-infrared spectra, as well as other portions of the electromagnetic spectrum, can be utilized and are known to those skilled in the art. For example, light sources may be continuum lamps such as a deuterium or xenon arc lamp for generation of ultraviolet light and/or a tungsten halogen lamp for generation of visible/near-infrared excitation. These light sources provide a broad emission range and the spectral bandwidth for specific excitation wavelengths may be reduced using optical interference filters, prisms and/or optical gratings, as are well known in the art.

Alternatively, a plurality of narrowband light sources, such as light emitting diodes and/or lasers, may be spatially multiplexed to provide a multi-wavelength excitation source. For example, light emitting diodes are available from 190 nm to in excess of 900 nm and the sources have a spectral bandwidth of 20-40 nm (full width at half maximum). Lasers are available in discrete wavelengths from the ultraviolet to the near-infrared and can be employed in multiplexing methods well known to those skilled in the art.

The spectral selectivity of any of the light sources may be improved by using spectral discrimination means such as a scanning monochromator. Other methods of discrimination may be utilized, as known to those of skill in the art, such as an acousto-optic tunable filter, liquid crystal tunable filter, an array of optical interference filters, prism spectrograph, etc., and in any combination. A consideration in selecting the spectral discriminator takes into account the range of tunability as well as the level of selectivity. By way of illustration, for example, a discriminator might utilize the wavelength range of 300-800 nm with a selectivity of 10 nm. These parameters generally determine the optimum technology necessary to achieve the tunability range as well as the selectivity.

Typically, the light source results in the excitation of the sample, followed by measurement of the emission of fluorescence of the sample at predetermined time points or continuously. Similarly, the reflected light from interaction of the excitation source with the sample may be measured to provide pertinent data for detection and/or characterization.

The emission from the sample may be measured by any suitable means of spectral discrimination, and in some embodiments employs a spectrometer. The spectrometer may be a scanning monochromator that detects specific emission wavelengths whereby the output from the monochromator is detected by a photomultiplier tube and/or the spectrometer may be configured as an imaging spectrograph whereby the output is detected by an imaging detector array such as a charge-coupled device (CCD) detector array. In one embodiment, a discriminator allows the observation of the fluorescence and/or scattering signal by a photodetection means (such as a photomultiplier tube, avalanche photodiode, CCD detector array, and/or electron multiplying charge coupled device (EMCCD) detector array).

The spectroscopic technique is used to obtain measurements that are preferably provided as Excitation-Emission Matrix (EEM) measurements. As used herein, EEM is defined as the luminescent spectral emission intensity of fluorescent substances as a function of both excitation and emission wavelength, and includes a full spectrum or a subset thereof, where a subset may contain a single or multiple excitation/emission pair(s). Additionally, a cross section of the EEM with a fixed excitation wavelength may be used to show the emission spectra for a specific excitation wavelength, and a cross section of the EEM with a fixed emission wavelength may be used to show the excitation spectra for a sample. In one embodiment, multiple EEMs are measured at more than one specific excitation-emission wavelength pair, e.g., at least at 2, 3, 4, 5, 6, 7, 8, 9, 10, or more specific excitation-emission wavelength pairs. For example, one or more EEMs may be taken at wavelengths that detect the resistance-determining affinity ligand while one or more additional EEMs are taken at wavelengths that detect intrinsic properties of the microorganism, such as Rayleigh scattering points (260-580 nm), tryptophan (285/350 nm), collagen (305/315-330 nm), NADH (345/460 nm), and flavin (460/520 nm).

In accordance with one embodiment of the invention, it has been found that a front-face fluorescence spectroscopy provides an advantage in measuring the fluorescence and/or reflectance properties of highly scattering and highly quenching samples. The front-face method is a particularly useful spectroscopic method because this configuration is less affected by the interfering components of blood and microbiological culture media. The optical surface of the container may be illuminated at such an angle as to provide acceptable results as known to those skilled in the art, (e.g., Eisinger, J., and J. Flores, "Front-face fluorometry of liquid samples," *Anal. Biochem.* 94:15-21 (1983)). In one embodiment, the system is designed such that the spectroscopic system measures diffuse reflected light at a minimum of one fixed angle in addition to measuring emitted fluorescence at a minimum of one fixed angle.

According to the invention, control measurements are taken for known microorganisms (antibiotic-sensitive and/or antibiotic resistant), thus allowing for correlation of measured test data with characterization of the microorganisms of interest using various mathematical methods known to those skilled in the art. For example, the data from samples may be compared with the baseline or control measurements utilizing software systems known to one skilled in the art. More particularly, the data may be analyzed by a number of multivariate analysis methods, such as, for example, General Discriminant Analysis (GDA), Partial Least Squares Discriminant Analysis (PLSDA), Partial Least Squares Regression, Principal Component Analysis (PCA), Parallel Factor Analysis (PARAFAC), Neural Network Analysis (NNA) and/or Support Vector Machine (SVM). In one embodiment, the comparison step comprises comparing the amount of resistance-determining affinity ligand bound or binding affinity to either an antibiotic-sensitive or an antibiotic-resistant strain of the same microorganism. In another embodiment, the comparison step comprises comparing the amount of resistance-determining affinity ligand bound or binding affinity to both an antibiotic-sensitive and antibiotic-resistant strain of the same microorganism. In one embodiment, the amount bound or binding affinity to a known antibiotic-sensitive or antibiotic-resistant strain of the same microorganism is determined at the same time as the amount bound by the microorganism. In another embodiment, the amount bound or binding affinity to a known antibiotic-sensitive or antibiotic-resistant strain of the same microorganism has been previously determined The previously determined data may be present, e.g., in a database.

In addition to measuring the antibiotic resistance of microorganisms and optionally one or more intrinsic properties of microorganisms (such as intrinsic fluorescence), the methods of the present invention can further comprise the use of additional identifier agents to aid in the separation and/or characterization process. Agents that bind to specific microorganisms, such as affinity ligands, can be used to separate microorganisms, to identify a class or species of microorganism (e.g., through binding to a unique surface protein or receptor) and/or to identify a characteristic of the microorganism. Useful identifier agents or affinity ligands include, without limitation, monoclonal and polyclonal antibodies and fragments thereof (e.g., anti-Eap for *S. aureus* identification), nucleic acid probes, aptamers, peptide mimetics, phage-derived binding proteins, lectins, host defense peptides (e.g., defensins, cathelicidins, proteogrins, magainins), bacterocins (e.g., lantibiotics, such as nisin, mersacidin, epidermin, gallidermin, and plantaricin C, and class II peptides), bacteriophages, and dyes selective for nucleic acids, lipids, carbohydrates, polysaccharides or proteins, or any combination thereof. If the agent does not itself give out a detectable signal, the agent can be labeled to provide a detectable signal, such as by conjugating the agent to a marker (e.g., visible or fluorescent). Markers include, without limitation, fluorescent, luminescent, phosphorescent, radioactive, Raman-active, mass spectrometry-reactive and/or colorimetric compounds. The agent can be added to the microorganisms at any step in the methods of the invention, e.g., when the sample is obtained, during the contact step, during the separation step, and/or during the detection step. In some embodiments, the presence of the agent in the pellet can be determined during interrogation of the pellet. Other useful identifier agents include substrates for microbial enzymes, chelating agents, photosensitizing agent, quenching agent, reducing agent, oxidizing agent, buffer, acid, base, solvent, fixative, detergents, surfactants, disinfectants (eg. alcohols, bleach, hydrogen peroxide) and toxic compounds (eg. sodium azide, potassium cyanide) and metabolic inhibitors such as cyclohexamide, etc. Similarly, many fluorescent compounds for measuring microbial cell viability, metabolism and/or membrane potential may be used as an identifier agent in the present invention. As would be readily appreciated by one of skill in the art, the sensitivity of a particular microorganism to any compound affecting its physical state or metabolism, such as an antibiotic, could be rapidly ascertained by adding the compound to the sample, lysis buffer, density cushion or any mixture thereof.

In one aspect of the invention, the method can further comprise a step of recovering the pellet of microorganism/resistance-determining affinity ligand complexes and performing additional tests. In one embodiment, the pellet can be recovered by aspirating off the sample medium and/or binding mixture or composition and the density cushion. In another embodiment, the pellet can be recovered by inserting a syringe into the container and aspirating out the pellet while the sample medium and/or binding mixture or composition and density cushion remain intact. The recovered pellet can then be resuspended in a suitable medium, e.g., saline. Once resuspended, the microorganisms can be subject to any further tests that are desired, as would be known to those of skill in the art and as described above. In particular, any test requiring clean samples of microorganisms can be carried out with the resuspended microorganisms. In some embodiments, additional identification tests can be performed. Examples of identification tests include Vitek 2, amplified and non-amplified nucleic acid tests (NAT), chromogenic and latex agglutination assays, immunoassays, (e.g., employing labeled antibodies and/or other ligands), mass spectroscopy (e.g., MALDI-TOF mass spectroscopy) and/or other optical techniques such as infrared spectroscopy (FTIR) or Raman spectroscopy. Additional characterization tests can also be performed, such as drug resistance. The additional characterization may be part of a test that was started during the initial separation and characterization steps of the method.

In one aspect of the invention, some or all of the method steps can be automated. As used herein, the term "automated" means computer controlled. In one embodiment, the various fluorescence emission detection and correlation steps are automated, and the resulting information obtained from the methods is automatically used to populate a database. In further embodiments, other steps in the method, such as contact, separation, and/or detection, can also be automated. Automating the steps of the methods not only allows more samples to be tested more quickly, it also reduces the risks of human errors in handling samples that may contain harmful and/or infectious microorganisms.

In a further aspect, the invention relates to systems for identifying an antibiotic-resistant microorganism, comprising:
(a) a container comprising a microorganism or a sample containing the microorganism and a resistance-determining affinity ligand;
(b) a density cushion; and
(c) a spectrometer to provide a measurement;
wherein said measurement identifies said antibiotic-resistant microorganism that has been concentrated in said container by an in situ separation within said system. In another embodiment, the system comprises a centrifuge for separating the microorganism from unbound resistance-determining affinity ligand.

The present invention is further detailed in the following examples, which are offered by way of illustration and is not intended to limit the invention in any manner. Standard techniques well known in the art or the techniques specifically described below are utilized.

EXAMPLES

Example 1

Binding of BOCILLIN™-FL to MRSA and MSSA Strains

Two experimental approaches were used to test BOCILLIN™-FL (Molecular Probes, Invitrogen) binding to *S. aureus*: (1) treating cells with sodium hydroxide (NaOH), neutralizing, adding BOCILLIN™-FL, then separating the cells (harsh pretreatment); and (2) culturing cells with BOCILLIN™-FL, then separating the cells (metabolic labeling).

For the first method, *S. aureus* strains ATCC 25923 (Methicillin-Sensitive; MSSA) and D14906 (Methicillin-Resistant; MRSA) were cultured until exponential growth (6 hours) in tryptic soy broth (TSB). Samples of each suspension (0.9 ml in TSB) and 0.1 N NaOH (0.1 ml; ±20 μl 7.5% TRITON® X100-R) were vortexed for 5 seconds, then either neutralized immediately or after 1 minute by adding 1 M $KH_2PO_4$ (0.125 ml) and vortexing for 5 seconds. BOCILLIN™-FL (15 μl of 1.0 mg/ml) was added to the suspension, which was then vortexed, and incubated for 5 minutes at room temperature. Unbound BOCILLIN™-FL was removed by centrifuging the mixture over 0.2 ml of an oil blend optimized to separate microorganisms from culture media (1.0 part of Type DF microscope immersion oil+0.875 parts of Drakeol 5 mineral oil) at 10,000 rpm for 1 minute. The supernatant and oil layer were removed and the pellet resuspended in 3.0 ml PBS, pH 7.4. The sample was scanned in the FluoroLog-3 system at an excitation wavelength of 490 nm and the fluorescence emission at 510 nm was recorded.

The results are shown in Table 1. Treatment of cells at pH 12 for 5 seconds resulted in more BOCILLINT™-FL binding to MSSA cells than to MRSA cells (condition a=2.3 ratio). No benefit was obtained by including Triton X-100 in the reaction mixture. Increasing the treatment of the cells at pH 12 to 60 seconds provided no benefit, and led to loss of cells.

TABLE 1

| Conditions | MSSA (25923) | MRSA (D14906) | MSSA/MRSA Ratio |
|---|---|---|---|
| a = 5" at pH 12 | $3.7 \times 10^6$ | $1.6 \times 10^6$ | 2.3 |
| b = 60" at pH 12 | $1.0 \times 10^6$ | $0.9 \times 10^6$ | 1.1 |
| c = 5" at pH 12 + TX100 | $0.9 \times 10^6$ | $0.6 \times 10^6$ | 1.5 |
| d = 60" at pH 12 + TX100 | $0.8 \times 10^6$ | $0.4 \times 10^6$ | 2.0 |

For the second method, the two bacterial suspensions (13 ml) were mixed with BOCILLINT™-FL (175 μl of 1.0 mg/ml stock). The mixtures were aliquoted in 1.0 ml samples into microfuge tubes containing 0.2 ml of oil blend. The tubes were incubated at 37° C. for various time-points (keeping 1 set of tubes on ice for the $T_0$ time-point). One set of tubes was removed at 30 minutes and the cells separated from free BOCILLINT™-FL by washing twice with PBS. One set of tubes was removed at 30, 52, 68, and 86 minutes and the cells separated from free BOCILLIN™-FL by centrifugation through the oil blend. The cells were recovered and resuspended in 3 ml PBS. The samples were scanned in the FluoroLog-3 system at an excitation wavelength of 490 nm and the fluorescence emission at 510 nm was recorded.

The results are shown in Table 2 (raw data) and FIG. 1 (normalized data). The MRSA strain bound 2-7 fold less BOCILLIN™-FL than the MSSA strain (Table 2), or 3-4 fold less when estimated on a per cell basis by normalizing the BOCILLIN™-FL signal to the microbial tryptophan signal (FIG. 1). The largest difference between the MRSA and MSSA strains occurred after about 60 minutes of culture at 37° C. Centrifugation of bacteria through the oil blend gave higher levels of BOCILLIN™-FL binding than washing twice with PBS, although higher background signals were observed (at $T_0$) with the oil-based separation method.

TABLE 2

| Assay Condition | Separation Method | MSSA (25923) | MRSA (D14906) | MSSA/ MRSA Ratio |
|---|---|---|---|---|
| $T_0$ (ice) | Oil | 2,745,600 | 1,163,240 | 2.36 |
| 30' at 37° C. | washed × 2 (PBS) | 410,830 | 206,250 | 2.00 |
| 30' at 37° C. | Oil | 1,831,790 | 326.790 | 5.60 |

TABLE 2-continued

| Assay Condition | Separation Method | MSSA (25923) | MRSA (D14906) | MSSA/ MRSA Ratio |
|---|---|---|---|---|
| 52' at 37° C. | Oil | 1,941,930 | 363,000 | 5.35 |
| 68' at 37° C. | Oil | 2,481,450 | 346,270 | 7.17 |
| 86' at 37° C. | Oil | 2,285,980 | 510,150 | 4.48 |

Example 2

Time Course Experiment

Samples of S. aureus strains ATCC 25923 (MSSA) and D14906 (MRSA) were grown in BacT/ALERT SA culture media at 37° C. until exponential growth was reached (8-10 hours). The OD 660 nm of each culture was measured and both suspensions were adjusted to 0.50 with pre-warmed SA media. BOCILLINT™-FL was diluted in pre-warmed SA media, filtered through a 0.2 µm filter and kept at 37° C. Samples of the bacteria (9.0 ml) were mixed with 1.0 ml of 100 µM BOCILLINT™-FL, mixed well, and dispensed as ten 1.0 ml aliquots into microfuge tubes containing 0.2 ml of the same oil blend used in Example 1. All tubes except the $T_0$ tube were placed at 37° C. Tubes were removed and processed at 6, 11, 16, 22, 45, 60, 75, and 91 minutes. Each tube was centrifuged for 1 minute, the supernatant was aspirated, and the pellet was resuspended in 0.1 ml PBS and then added to 3.0 ml PBS in an acrylic cuvette. The sample was scanned in the FluoroLog-3 system at an excitation wavelength of 490 nm and the fluorescence emission at 510 nm was recorded.

Figure 2:
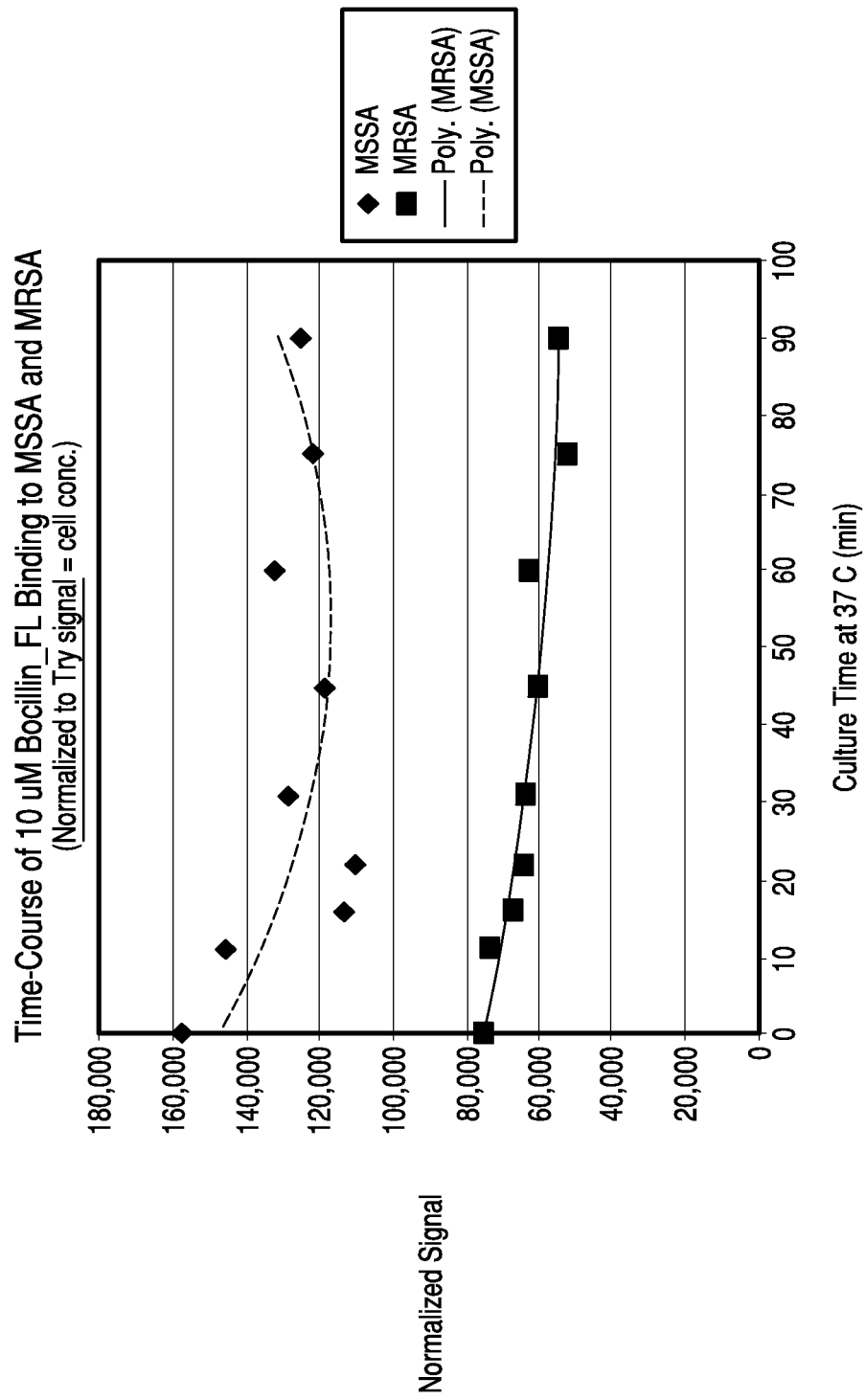
FIG. 2 shows the time course of BOCILLINT™-FL binding to MSSA and MRSA strains.

Binding of BOCILLINT™-FL to S. aureus strains, as assessed by the oil method, occurred quickly (FIG. 2). Data was plotted using a second order polynomial curve fit. Maximal binding was measured after as little as 5 min at room temperature (i.e. the $T_0$ tube). At this concentration of BOCILLINT™-FL, the MSSA strain bound approximately 2-3 times more BOCILLINT™-FL than the MRSA strain on a per cell basis, irrespective of the culture time.

Example 3

Titration of BOCILLIN™-FL

Samples of S. aureus strains ATCC 25923 (MSSA) and D14906 (MRSA) were grown in BacT/ALERT SA culture media at 37° C. for about 6 hours until an OD 660 nm of about 0.35 was reached. Dilutions of BOCILLINT™-FL (0.1 ml) were prepared in SA medium and placed into culture tubes. Samples of the bacterial suspension (0.9 ml) were added to the tubes and mixed. The tubes were capped and placed in a 37° C. incubator for 60 minutes. Samples (1.0 ml) were transferred to microfuge tubes containing 0.2 ml of the same oil blend used in Example 1, centrifuged for 1 minute, aspirated, and the pellet was resuspended in 0.1 ml PBS and then added to 3.0 ml PBS, pH 7.4 in an acrylic cuvette. The sample was scanned in the FluoroLog-3 system at an excitation wavelength of 490 nm and the fluorescence emission at 510 nm was recorded.

Figure 3:
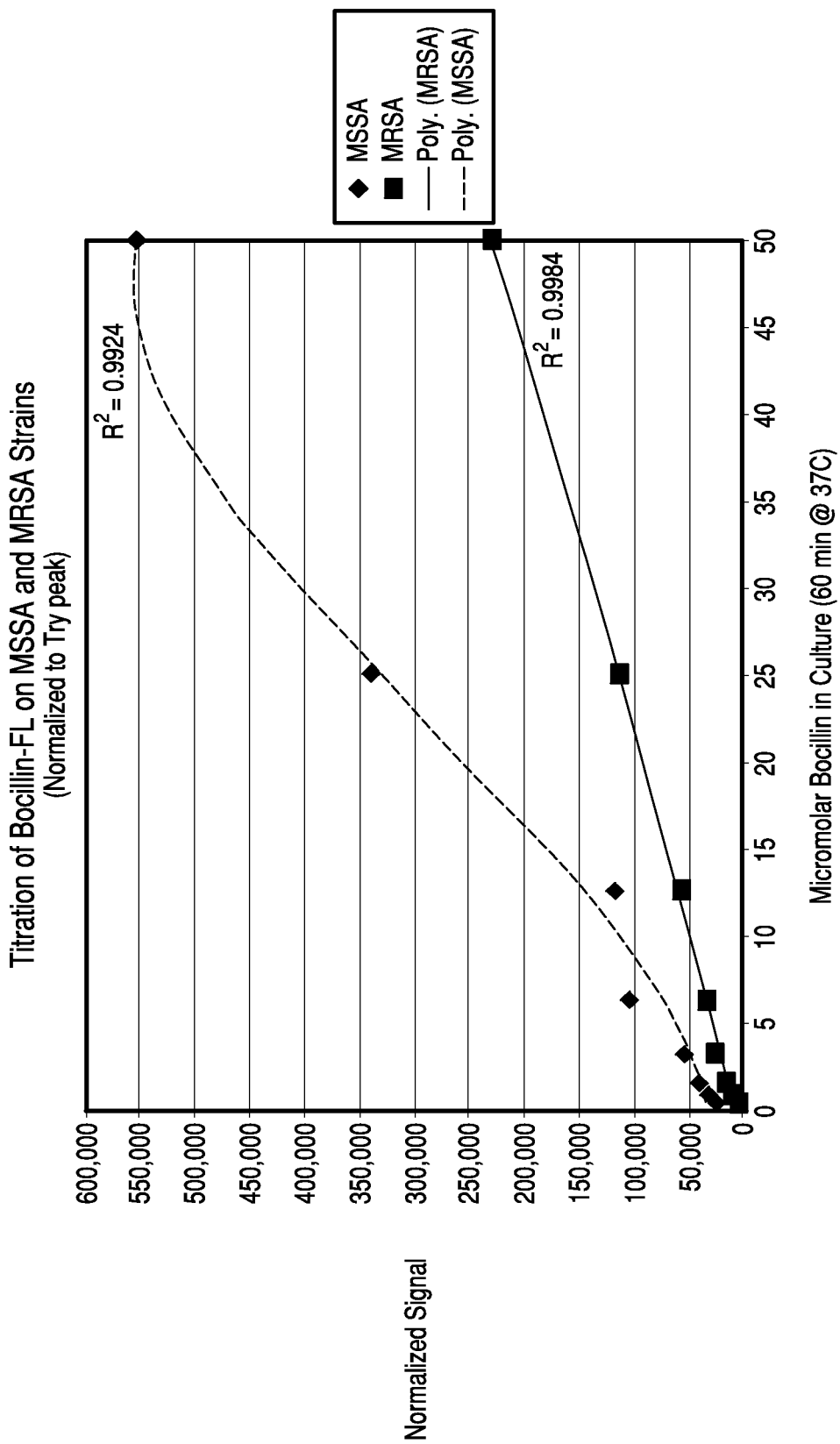
FIG. 3 shows the titration of BOCILLINT™-FL binding to MSSA and MRSA strains.

The MSSA strain bound 2-4 fold more BOCILLINT™-FL than the MRSA strain on a per cell basis, depending on the BOCILLINT™-FL concentration (FIG. 3). Data was plotted using a second order polynomial curve fit. The MSSA binding curve was biphasic. An initial saturable curve existed from 0.5 to about 10 µM, followed by a second phase with increased binding. At about 5 µM BOCILLINT™-FL, there was a 3-fold difference between the MSSA and MRSA strains. At about 0.5 µM BOCILLINT™-FL, there was a 4-fold difference between the MSSA and MRSA strains.

Example 4

Assessment of a Panel of MRSA and MSSA Strains

Twenty different strains of S. aureus (10 MRSA and 10 MSSA strains, confirmed with cefoxitin discs and Vitek-2) were propagated. A loopful of growth (1 µL) was removed from 24-hour plates and suspended in BacT/ALERT SA culture media (8 ml in a glass screw-capped tube). The tubes were vortexed well and incubated at 36° C. for 6 hours. The OD of each suspension was measured at 660 nm and adjusted to approximately the same density (0.50-0.75 OD; sample #12166 was only 0.28). 50 µM BOCILLINT™-FL (0.1 ml) was placed into each of 20 labeled microfuge tubes. A sample of each strain (0.9 ml) was added to each tube, mixed, and incubated at 37° C. for 30 minutes. The reaction mixture was then removed and added to a second set of tubes containing 0.2 ml of an oil blend (1.000 part type DF immersion oil plus 0.875 part Drakeol 5 mineral oil). The tubes were centrifuged for 2 minutes at 10,000 rpm in an A-8-11 rotor (Eppendorf 5417R). The supernatant and most of the oil was aspirated with a vacuum device. The remaining oil was removed using a Gilson P200 tip and the pellet was resuspended in 100 µl PBS. The cells were transferred to an acrylic cuvette containing 3 ml PBS and read in the FluoroLog 3 system using the FluoroScan "Bocillin" points listed in Table 3. Additionally, Vitek AST cards were run on each of the 20 isolates (from the same 24 hour plates).

TABLE 3

| Rayleigh pts | 260-580 |
|---|---|
| Tryptophan peak | 285/350 |
| MRSA/MRSE | 305/315-330 |
| Collagen | 320/405 |
| NADH | 345/460 |
| Flavin | 460/520 |
| BOCILLIN ™-FL | 490/510 |

Figure 4:
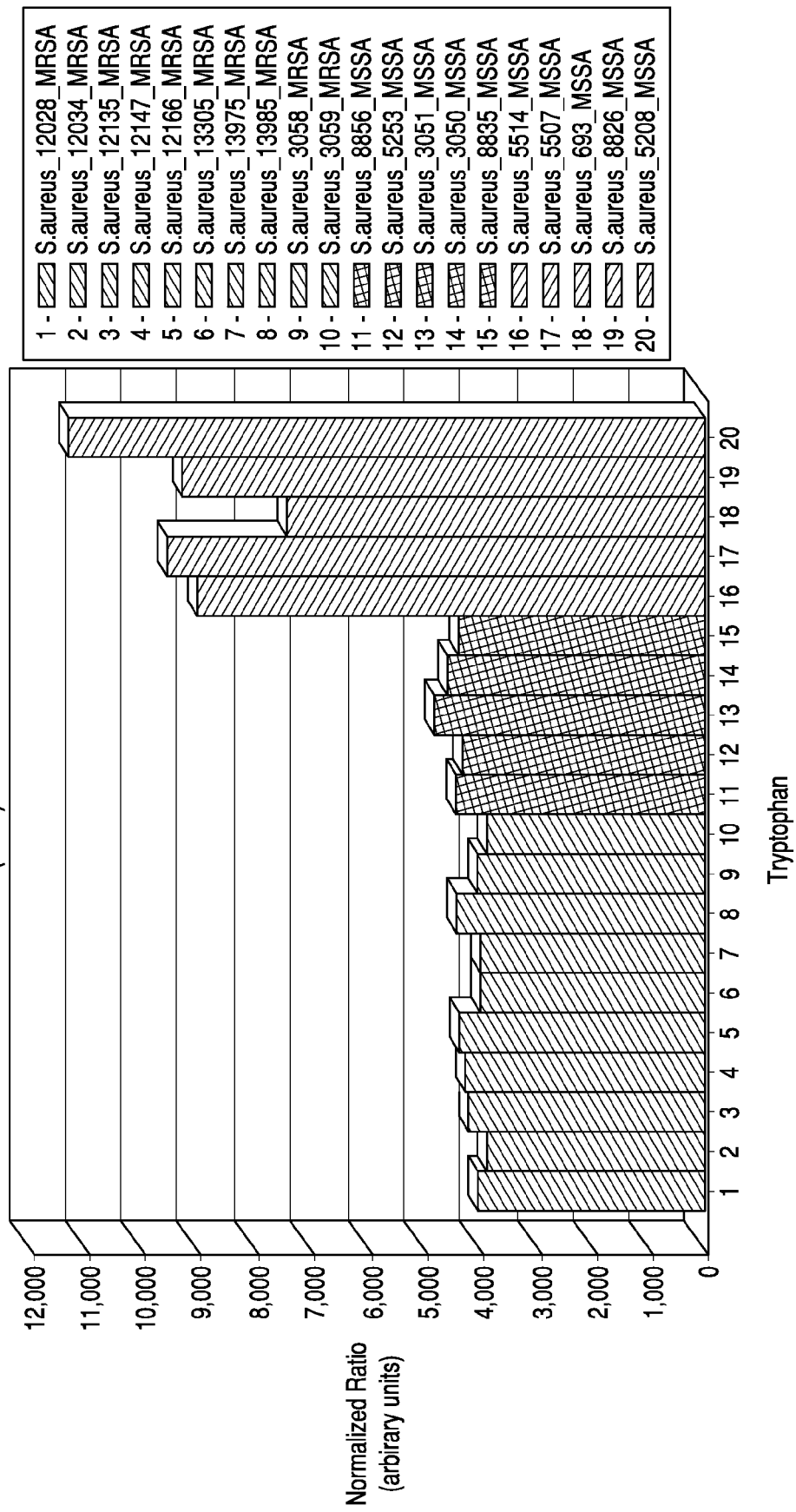
FIG. 4 shows the binding of BOCILLINT™-FL to different MSSA and MRSA strains.

Optimal results were obtained when the BOCILLINT™-FL signal (Ex490_Em510) was normalized to the tryptophan signal (Ex285_Em350). The five benzyl-penicillin sensitive strains bound over twice the amount of BOCILLINT™-FL than the fifteen benzyl-penicillin resistant strains (FIG. 4). This result demonstrates that the assay is specific and correlates with the observed Vitek MIC. 5 of the 10 oxacillin-sensitive (MSSA) strains bound higher levels of BOCILLINT™-FL for an MRSA sensitivity of 50% and a specificity of 100%. These 5 strains were classified as benzyl-penicillin resistant and oxacillin sensitive by Vitek cards and 3/5 strains had an oxacillin MIC of 0.5.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

Example 5

Determining Resistance Status of a Microorganism Indirectly Through Changes in Intrinsic Fluorescence and/or Membrane Integrity Four strains of E. faecium were selected for this study. Two were VRE with vancomycin MIC's of >32 µg/mL by VITEK 2 (#12406, #13185) and two were VSE with vancomycin MIC's of >0.5 μg/mL by VITEK 2 (#14054, #12480).

For each test strain, a 1 μl loopful of colonies from a 24-48 hour plate was suspended in 10-12 mL of BacT/ALERT SA media and cultured for 4-9 hours at 37° C. Samples of each log phase culture were then incubated with 0, 0.25, 2.5 and 12.5 μg/mL of vancomycin-HCl in combination with 1:5000 dilution of stock Sytox Green, a viable cell impermeant DNA stain (Molecular Probes, cat #S7020), for a period of 4 hours at 37° C. Aliquots of the cultures were removed for analysis immediately (T0) and after 1, 2.5 and 4 hours.

At the appropriate time-point, 0.5 mL aliquots of the cultures (0.5 mL) were overlaid on a density cushion composed of 24% w/v CsCl in 10 mM Hepes, pH 7.4 and 0.005% Pluronic F-108 contained in custom-made optical centrifugation tubes as disclosed in related U.S. patent application Ser. No. 12/589,969, entitled "Separation Device for Use in the Separation, Characterization and/or Identification of Microorganisms", filed Oct. 30, 2009. The tubes were sealed and centrifuged at 10,000 rpm for 2 minutes to separate intact microorganisms from the culture medium and unbound chemicals. The tubes were then placed into a custom-built tube holder directly onto a fiber optic probe built into the base. The probe was attached to a FluoroLog 3 spectrofluorimeter. The tube was interrogated through its UV-transperent base, and fluorescence and diffuse reflectance readings collected.

The results for microbial NADH fluorescence (Ex340 nm/Em440 nm) are given in Table 4. At vancomycin levels that were inhibitory to the two VSE strains (2.5 and 12.5 ng/mL), cellular NADH levels gradually declined over time. In contrast, NADH levels in the two VRE strains treated with the same vancomycin levels rose after approximately 1 hour in culture and continued to rise over the 4-hour culture period. One VRE strain (#12406) had a longer delay in NADH production, which correlated with an influx of Sytox Green over this period.

The results for microbial tryptophan fluorescence (Ex300 nm/Em360 nm) are given in Table 5. At vancomycin levels that were inhibitory to the two VSE strains (2.5 and 12.5 ng/mL), cellular tryptophan levels remained stable over time. In contrast, tryptophan levels in the two VRE strains treated with the same vancomycin levels rose slowly over the 4-hour culture period.

The results for Sytox Green (Ex510 nm/Em530 nm) are given in Table 6 and are expressed as a ratio of Sytox Green to NADH fluorescence to compensate for viable cell biomass. The data demonstrates that one of the two VRE strains (#14206) was being affected by vancomycin over the first 2 hours of culture and then began to recover. This finding indicates that this strain required a few hours of co-culture with vancomycin for the resistant phenotype to dominate this particular population. This behavior likely indicates that this strain possess inducible resistance that was detected by this method.

This experiment demonstrates that measuring changes in the intrinsic fluorescence of microbial cells co-cultured with antibiotic can be used to rapidly determine if an organism is resistant to the antibiotic. Furthermore, the addition of fluorescent dyes to monitor the integrity of the cell membranes in the microbial population under test provides valuable information on the viability and induction of resistance by a microbial population.

TABLE 4

Temporal Changes in Microbial NADH in Vancomycin Sensitive and Resistant Strains

| Strain # | Vanc. (μg/mL) | Zero time | 1 hour | 2.5 hour | 4 hour |
|---|---|---|---|---|---|
| 12406 (VRE) | 0 | 176,514 | 514,368 | 690,324 | 588,224 |
| 12406 (VRE) | 0.25 | 207,307 | 616,448 | 703,451 | 598,853 |
| 12406 (VRE) | 2.5 | 440,416 | 253,323 | 573,926 | 931,786 |
| 12406 (VRE) | 12.5 | 172,372 | 207,520 | 279,170 | 765,401 |
| 14054 (VSE) | 0 | 385,933 | 323,090 | 710,289 | 479,486 |
| 14054 (VSE) | 0.25 | 449,599 | 298,998 | 733,656 | 534,989 |
| 14054 (VSE) | 2.5 | 290,986 | 195,152 | 349,287 | 96,954 |
| 14054 (VSE) | 12.5 | 248,332 | 188,273 | 128,491 | 109,080 |
| 13185 (VRE) | 0 | 345,051 | 516,677 | 564,287 | 624,663 |
| 13185 (VRE) | 0.25 | 316,618 | 708,442 | 496,545 | 627,392 |
| 13185 (VRE) | 2.5 | 256,533 | 237,463 | 965,305 | 782,908 |
| 13185 (VRE) | 12.5 | 234,554 | 226,769 | 775,629 | 710,100 |
| 12480 (VSE) | 0 | 201,074 | 487,559 | 477,522 | 500,649 |
| 12480 (VSE) | 0.25 | 184,649 | 271,470 | 500,618 | 483,445 |
| 12480 (VSE) | 2.5 | 221,692 | 254,828 | 149,686 | 100,931 |
| 12480 (VSE) | 12.5 | 178,982 | 210,963 | 171,994 | 127,042 |

TABLE 5

Temporal Changes in Microbial Tryptophan in Vancomycin Sensitive and Resistant Strains

| Strain # | Vanc. (μg/mL) | Zero time | 1 hour | 2.5 hour | 4 hour |
|---|---|---|---|---|---|
| 12406 (VRE) | 0 | 451,075 | 661,339 | 761,500 | 869,806 |
| 12406 (VRE) | 0.25 | 463,942 | 666,793 | 679,880 | 800,658 |
| 12406 (VRE) | 2.5 | 425,860 | 560,948 | 656,768 | 651,886 |
| 12406 (VRE) | 12.5 | 463,985 | 433,269 | 560,607 | 738,461 |
| 14054 (VSE) | 0 | 395,244 | 583,435 | 673,219 | 826,840 |
| 14054 (VSE) | 0.25 | 387,455 | 601,874 | 670,217 | 808,566 |
| 14054 (VSE) | 2.5 | 369,386 | 431,754 | 437,349 | 428,796 |
| 14054 (VSE) | 12.5 | 384,046 | 421,876 | 387,066 | 403,029 |
| 13185 (VRE) | 0 | 535,014 | 565,301 | 852,060 | 923,848 |
| 13185 (VRE) | 0.25 | 546,862 | 557,453 | 809,317 | 880,899 |
| 13185 (VRE) | 2.5 | 531,239 | 569,043 | 489,661 | 868,768 |
| 13185 (VRE) | 12.5 | 537,160 | 579,537 | 537,067 | 782,106 |
| 12480 (VSE) | 0 | 405,128 | 497,676 | 662,021 | 745,217 |
| 12480 (VSE) | 0.25 | 425,539 | 460,266 | 678,352 | 706,797 |
| 12480 (VSE) | 2.5 | 361,962 | 438,541 | 466,525 | 416,780 |
| 12480 (VSE) | 12.5 | 389,264 | 428,402 | 455,446 | 438,978 |

TABLE 6

Temporal Changes in Sytox Green Influx into Vancomycin Sensitive and Resistant Strains

| Strain # | Vanc. (μg/mL) | Zero time | 1 hour | 2.5 hour | 4 hour |
|---|---|---|---|---|---|
| 12406 (VRE) | 0 | 0.4 | 0.7 | 0.4 | 0.5 |
| 12406 (VRE) | 0.25 | 0.3 | 0.6 | 0.4 | 0.5 |
| 12406 (VRE) | 2.5 | 0.2 | 17.7 | 4.5 | 1.2 |
| 12406 (VRE) | 12.5 | 0.4 | 19.8 | 14.6 | 1.9 |
| 14054 (VSE) | 0 | 0.6 | 1.2 | 0.6 | 1.0 |
| 14054 (VSE) | 0.25 | 0.4 | 1.4 | 0.6 | 0.8 |
| 14054 (VSE) | 2.5 | 0.7 | 30.1 | 17.6 | 43.4 |
| 14054 (VSE) | 12.5 | 0.9 | 14.1 | 39.1 | 35.4 |
| 13185 (VRE) | 0 | 0.2 | 0.4 | 0.3 | 0.3 |
| 13185 (VRE) | 0.25 | 0.3 | 0.3 | 0.3 | 0.2 |
| 13185 (VRE) | 2.5 | 0.3 | 1.8 | 0.4 | 0.3 |
| 13185 (VRE) | 12.5 | 0.4 | 1.4 | 0.5 | 0.3 |
| 12480 (VSE) | 0 | 0.2 | 0.5 | 0.7 | 0.5 |

TABLE 6-continued

Temporal Changes in Sytox Green Influx into
Vancomycin Sensitive and Resistant Strains

| Strain # | Vanc. (µg/mL) | Zero time | 1 hour | 2.5 hour | 4 hour |
|---|---|---|---|---|---|
| 12480 (VSE) | 0.25 | 0.3 | 1.0 | 0.6 | 0.6 |
| 12480 (VSE) | 2.5 | 0.2 | 6.7 | 20.9 | 20.8 |
| 12480 (VSE) | 12.5 | 0.2 | 1.5 | 7.8 | 8.7 |

That which is claimed is:

1. A method for determining the antibiotic-resistance status of a microorganism, comprising:
   (a) contacting intact microorganisms with a resistance-determining affinity ligand under conditions whereby a microorganism/resistance-determining affinity ligand complex is formed and wherein said resistance-determining affinity ligand is not an antibody or antibody fragment;
   (b) layering said microorganism/resistance-determining affinity ligand complex on a density cushion in a container and centrifuging said container to separate said microorganism/resistance-determining affinity ligand complex formed in (a) from unbound resistance-determining affinity ligand;
   (c) determining the amount of resistance-determining affinity ligand bound to the intact microorganisms in the microorganism/resistance-determining affinity ligand complex; and
   (d) comparing the amount of resistance-determining affinity ligand bound to the intact microorganisms in the microorganism/resistance-determining affinity ligand complex to the amount of resistance-determining affinity ligand bound by a known antibiotic-sensitive or antibiotic-resistant strain of the same microorganism or a population of known antibiotic-sensitive or antibiotic-resistant strains;
   wherein if the intact microorganisms in the microorganism/resistance-determining affinity ligand complex binds a different amount of resistance-determining affinity ligand than is bound by the antibiotic-sensitive microorganism or the intact microorganisms in the microorganism/resistance-determining affinity ligand complex binds the same amount of resistance-determining affinity ligand as is bound by the antibiotic-resistant microorganism, the microorganism is identified as antibiotic-resistant, and wherein said method is carried out in less than about 240 minutes.

2. The method of claim 1, wherein one or more of steps (a), (b), (c), and/or (d) are carried out in a sealed container.

3. The method of claim 1, wherein the resistance-determining affinity ligand is selected from the group consisting of antibiotics, nucleic acid probes, enzyme substrates, aptamers, peptide mimetics, phage-derived binding proteins, lectins, host defense peptides, bacterocins, bacteriophages, dyes selective for nucleic acids, lipids, carbohydrates, polysaccharides, proteins, and combinations thereof.

4. The method of claim 1, wherein the resistance-determining affinity ligand is an antibiotic.

5. The method of claim 1, wherein the resistance-determining affinity ligand is a β-lactam antibiotic or a glycopeptide antibiotic.

6. The method of claim 1, wherein the resistance-determining affinity ligand comprises a detectable label.

7. The method of claim 6, wherein the detectable label is a fluorescent, luminescent, phosphorescent, radioactive, Raman-active, mass spectrometry-reactive and/or colorimetric compound label.

8. The method of claim 1, wherein the microorganism is in a clinical or non-clinical sample.

9. The method of claim 8, wherein the sample is from a positive blood culture.

10. The method of claim 1, wherein the sample comprising the microorganism is treated to selectively lyse any non-microbial cells that may be present in the sample prior to the separation step (b).

11. The method of claim 1, wherein said density cushion comprises one or more of microscope immersion oil, mineral oil, silicone oil, fluorosilicone oil, silicone gel, colloidal silica, iodinated contrast agents, sucrose, diatrizoate-dextran, carboxymethyl cellulose, hydroxypropylmethyl cellulose, polyethylene oxide (high molecular weight), polyoxyalkylene ether, polyacrylic acid, cross-linked polyvinyl alcohol, cross-linked polyvinyl pyrrolidine, PEG methyl ether methacrylate, pectin, agarose, xanthan, gellan, Gellan Gum, sorbitol, a sucrose and epichlorohydrin copolymer, glycerol, dextran, glycogen, cesium chloride, perfluorocarbon fluids, and/or hydrofluorocarbon fluid in any combination.

12. The method of claim 1, wherein said density cushion has a density of about 1.025 to about 1.120 g/ml.

13. The method of claim 1, wherein said container comprises an optical window on the bottom, top and/or one or more side of the container and wherein said optical window is transparent to at least a portion of the near infrared, ultraviolet, and/or visible light spectrum.

14. The method of claim 1, wherein said determining step (c) comprises spectroscopy.

15. The method of claim 14, wherein said spectroscopy is selected from the group consisting of fluorescence spectroscopy, diffuse reflectance spectroscopy, adsorption and transmission spectroscopy, infrared spectroscopy, terahertz spectroscopy, Raman spectroscopy, surface enhanced Raman spectroscopy, spacially-offset Raman spectroscopy, resonance Raman spectroscopy, and any combination thereof.

16. The method of claim 14, wherein said spectroscopy is front face fluorescence spectroscopy.

17. The method of claim 14, wherein said spectroscopy comprises determining an excitation-emission matrix (EEM).

18. The method of claim 17, wherein said EEM comprises at least two different wavelengths.

19. The method of claim 17, wherein said EEM is compared to a database of EEMs of known microorganisms.

20. The method of claim 1, wherein the amount of resistance-determining affinity ligand bound is determined on a per cell basis by comparing the amount bound to an intrinsic property of the microorganism.

21. The method of claim 20, wherein the intrinsic property is intrinsic fluorescence.

22. The method of claim 1, wherein step (c) comprises a step of recovering the microorganism to produce a recovered microorganism.

23. The method of claim 1, wherein step (d) comprises comparing the amount of resistance-determining affinity ligand bound to the amount of resistance-determining affinity ligand bound by both an antibiotic-sensitive and antibiotic-resistant strain of the same microorganism.

24. The method of claim 1, wherein the amount bound by a known antibiotic-sensitive or antibiotic-resistant strain of the same microorganism has been previously determined.

25. The method of claim 1, wherein the method is at least partially automated.

26. A method for determining the antibiotic-resistance status of a microorganism, comprising:
(a) contacting intact microorganisms with a resistance-determining affinity ligand under conditions whereby a microorganism/resistance-determining affinity ligand complex is formed, wherein said resistance-determining affinity ligand is not an antibody or antibody fragment;
(b) layering said microorganism/resistance-determining affinity ligand complex on a density cushion in a container and centrifuging said container to separate said microorganism/resistance-determining affinity ligand complex formed in (a) from unbound resistance-determining affinity ligand;
(c) determining the binding affinity of the resistance-determining affinity ligand to said intact microorganisms in the microorganism/resistance-determining affinity ligand complex; and
(d) comparing the binding affinity of the resistance-determining affinity ligand to said intact microorganisms in the microorganism/resistance-determining affinity ligand complex to the binding affinity of resistance-determining affinity ligand to a known antibiotic-sensitive or antibiotic-resistant strain of the same microorganism or a population of known antibiotic-sensitive or antibiotic-resistant strains;
wherein if said intact microorganisms in the microorganism/resistance-determining affinity ligand complex exhibits a different binding affinity of resistance-determining affinity ligand than the binding affinity exhibited by the antibiotic-sensitive microorganism or said intact microorganisms in the microorganism/resistance-determining affinity ligand complex exhibits the same binding affinity of resistance-determining affinity ligand as is exhibited by the antibiotic-resistant microorganism, the microorganism is identified as antibiotic-resistant, and wherein said method is carried out in less than 240 minutes.

27. A method for determining the antibiotic-resistance status of a microorganism, comprising:
(a) obtaining a test sample known to contain or that may contain intact microorganisms;
(b) contacting said intact microorganisms in the test sample with a resistance-determining affinity ligand under conditions whereby a microorganism/ resistance-determining affinity ligand complex is formed, wherein said resistance-determining affinity ligand is not an antibody or antibody fragment;
(c) optionally adding one or more fluorescent dyes that measure cell metabolism or membrane integrity;
(d) optionally selectively lysing any non-microbial cells that may be present in the sample to produce a lysed sample;
(e) layering said microorganism/resistance-determining affinity ligand complex on a density cushion in a container and centrifuging said container to separate said microorganism/resistance-determining affinity ligand complex from other components of said test sample, or said lysed sample, to form a pellet of intact microorganisms;
(f) interrogating the pellet to produce measurements of the microorganism;
(g) determining the antibiotic-resistance status of said intact microorganisms in the test sample by comparison of the measurements with measurements taken, or predicted, for antibiotic-resistant and/or antibiotic-susceptible microorganisms of the same species, and wherein said method is carried out in less than 240 minutes.

28. The method of claim 27, wherein one or more fluorescent dyes are added in step (c).

29. The method of claim 27, wherein said antibiotic-resistance determination in step (g) is determined to be induced resistance.

30. The method of claim 27, wherein said interrogation step (f) comprises interrogation by spectroscopy.

31. The method of claim 30, wherein said spectroscopy is selected from the group consisting of fluorescence spectroscopy, diffuse reflectance spectroscopy, adsorption and transmission spectroscopy, infrared spectroscopy, terahertz spectroscopy, Raman spectroscopy, surface enhanced Raman spectroscopy, spacially-offset Raman spectroscopy, resonance Raman spectroscopy, and any combination thereof.

* * * * *